US010294214B2

(12) United States Patent
Cone et al.

(10) Patent No.: US 10,294,214 B2
(45) Date of Patent: May 21, 2019

(54) POSITIVE ALLOSTERIC MODULATORS OF HUMAN MELANOCORTIN-4 RECEPTOR

(71) Applicants: Vanderbilt University, Nashville, TN (US); Glaxo Group Limited, Middlesex (GB); King's College London, London (GB)

(72) Inventors: Roger D. Cone, Nashville, TN (US); Michael J. Bishop, San Diego, CA (US); Eugene L. Stewart, Malvern, PA (US); Lawrence A. Wolfe, Collegeville, PA (US); Jaques Pantel, Paris (FR); Julien Sebag, Iowa City, IA (US); C. David Weaver, Nashville, TN (US); Savannah Williams, Nashville, TN (US); Helen Cox, London (GB); Iain Tough, London (GB); Luis Diaz Gimenez, Nashville, TN (US); Subramanian Baskaran, Cary, NC (US)

(73) Assignees: Vanderbilt University, Nashville, TN (US); King's College London, London (GB); Glaxo Group Limited, Middlesex (GB)

( * ) Notice: Subject to any disclaimer, the term of this patent is extended or adjusted under 35 U.S.C. 154(b) by 0 days.

(21) Appl. No.: 15/616,578

(22) Filed: Jun. 7, 2017

(65) Prior Publication Data
US 2017/0349571 A1    Dec. 7, 2017

Related U.S. Application Data

(60) Provisional application No. 62/346,892, filed on Jun. 7, 2016.

(51) Int. Cl.
| | |
|---|---|
| C07D 401/12 | (2006.01) |
| A61K 31/454 | (2006.01) |
| A61K 45/06 | (2006.01) |
| A61K 38/34 | (2006.01) |
| A61K 31/4439 | (2006.01) |
| A61K 31/496 | (2006.01) |
| A61K 31/5377 | (2006.01) |

(52) U.S. Cl.
CPC ........ *C07D 401/12* (2013.01); *A61K 31/4439* (2013.01); *A61K 31/454* (2013.01); *A61K 31/496* (2013.01); *A61K 31/5377* (2013.01); *A61K 38/34* (2013.01); *A61K 45/06* (2013.01)

(58) Field of Classification Search
CPC .................................................. C07D 401/12
See application file for complete search history.

(56) References Cited

FOREIGN PATENT DOCUMENTS

| WO | 99/64002 | 12/1999 |
|---|---|---|
| WO | 00/74679 | 12/2000 |
| WO | 01/70337 | 9/2001 |
| WO | 01/70708 | 9/2001 |
| WO | 01/91752 | 12/2001 |

OTHER PUBLICATIONS

STN-Chemical database registry #300587-09-1 entry for 1H-Indole-2-carboxylic acid, 3-[[2-(3-methyl-1-piperidinypacetyl]annino]-, methyl ester, ED Entered STN: Oct. 31, 2000, LC STN Files: CHEMCATS.*
IBS Products and Services "http://web.archive.org/web/20070529094927/http://www.ibscreen.com/products.shtml" dated May 29, 2007, accessed Aug. 27, 2014.*
Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*
Online "http://web.archive.org/web/20031225052253/http://www.specs.net/", accessed Apr. 1, 2015.*
Online "http://web.archive.org/web/20130122020518/http://www.chembridge.com/screening_libraries/" 2011, accessed Oct. 10, 2015.*
Online: "https://www.cas.org/support/documentation/chemical-substances/faqs" Accessed Sep. 14, 2018.*
Online: "https://www.cas.org/services/knowledge/chemist-consultation" Accessed Sep. 14, 2018.*
Online "https://www.cas.org/sites/default/files/documents/chemconsultform_v0.pdf" accessed Sep. 14, 2018.*
Online "https://www.cas.org/products/chemcats/chemical-suppliers/data-submission" accessed Sep. 14, 2018.*
STN-Chemical Database Registry # 372155-19-6 entry for 1H-Indole-2-carboxylic acid, 5-bromo-3-[[(4-phenyl-1-piperazinyl)acetyl] amino]-, methyl ester, ED Entered STN: Nov. 29, 2001.*
Asai, et al. (2013) Loss of function of the melanocortin 2 receptor accessory protein 2 is associated with mammalian obesity. Science 341(6143):275-278.
Asano, et al. (1984) Reconstitution of catecholamine-stimulated binding of guanosine 5'-O-(3-thiotriphosphate) to the stimulatory GTP-binding protein of adenylate cyclase. Biochem 23(23):5460-5467.
Butler, et al. (2001) Melanocortin-4 receptor is required for acute homeostatic responses to increased dietary fat. Nature Neuroscience 4(6):605-611.
Christopoulos (2014) Advances in G protein-coupled receptor allostery: from function to structure. Mol Pharmacol 86(5):463-478.
Cody, et al. (1999) Haplosufficiency of the melancortin-4 receptor gene in individuals with deletions of 18q. Hum Genet 105(5):424-427.
Cone (2005) Anatomy and regulation of the central melanocortin system. Nature neuroscience 8(5):571-578.
Da Silva, et al. (2008) Endogenous melanocortin system activity contributes to the elevated arterial pressure in spontaneously hypertensive rats. Hypertension 51(4):884-890.

(Continued)

*Primary Examiner* — David K O'Dell
(74) *Attorney, Agent, or Firm* — Meunier Carlin & Curfman LLC

(57) ABSTRACT

Disclosed herein are positive allosteric modulators of melanocortin receptor and methods of using such modulators.

3 Claims, 4 Drawing Sheets

(56) References Cited

OTHER PUBLICATIONS

Davey, et al. (2012) Positive and negative allosteric modulators promote biased signaling at the calcium-sensing receptor. Endocrinology 153(3):1232-1241.
Farooqi, et al. (2003) Clinical spectrum of obesity and mutations in the melanocortin 4 receptor gene. N Engl J Med 348(12): 1085-1095.
Fosgerau, et al. (2014) Novel alpha—MSH analog causes weight loss in obese rats and minipigs and improves insulin sensitivity. J Endocrinol 220(2):97-107.
Ghamari-Langroudi, et al. (2015) G-protein-independent coupling of MC4R to Kir7.1 in hypothalamic neurons. Nature doi: 10.1038/nature14051.
Greenfield, et al. (2009) Modulation of blood pressure by central melanocortinergic pathways. N Engl J Med 360(1):44-52.
Haqq, et al. (2003) Characterization of a novel binding partner of the melanocortin-4 receptor: attracting-like protein. Biochem J 376(Pt 3):595-605.
Hess, et al. (2008) Backbone cyclic peptidomimetic melanocortin-4 receptor agonist as a novel orally administrated drug lead for treating obesity. J Med Chem 51(4):1026-1034.
Huang, et al. (2003) Effects of manufacturing process variables on in vitro dissolution characteristics of extended-release tablets formulated with hydroxypropyl methylcellulose. Drug Dev Ind Pharm. 29:79.
Huszar, et al. (1997) Targeted disruption of the melanocortin-4 receptor results in obesity in mice. Cell 88:131-141.
Josep Agulleiro, et al. (2013) Melanocortin 4 receptor becomes an ACTH receptor by coexpression of melanocortin receptor accessory protein 2. Mol Endocrinol 27(11):1934-1945.
Joseph, et al. (2008) The 1,4-benzodiazepine-2,5-dione small molecule template results in melanocortin receptor agonists with nanomolar potencies. J Med Chem 51(5):1423-1431.
Khanvilkar, et al.,(2002) Influence of Hydroxypropyl Methylcellulose Mixture, Apparent Viscosity, and Tablet Hardness on Drug Release Using a 23 Full Factorial Design. Drug Dev. Ind. Pharm. 228:601.
Kievit, et al. (2012) Chronic treatment with a melanocortin-4 receptor agonist causes weight loss, reduces insulin resistance, and improves cardiovascular function in diet-induced obese rhesus macaques. Diabetes 62(2):490-497.
Kruse, et al. (2013) Activation and allosteric modulation of a muscarinic acetylcholine receptor. Nature 504(7478):101-106.
Maggi, et al. (2003) Photostability of extended-release matrix formulations Eur. J. Pharm Biopharm 55:99.
Mathiesen, et al. (2005) Identification of indole derivatives exclusively interfering with a G protein-independent signaling pathway of the prostaglandin D2 receptor CRTH2. Mol Pharmacol 68(2):393-402.
McGuinness, et al. (2009) Characterizing cannabinoid CB2 receptor ligands using DiscoveRx PathHunter beta-arrestin assay. J B iomol Screening 14(1):49-58.
Pantel, et al. (2011) Development of a high throughput screen for allosteric modulators of melanocortin-4 receptor signaling using a real time cAMP assay. Eur J Pharmacol 660:139-147.
Pearnchob, et al. (2003) Pharmaceutical Applications of Shellac: Moisture-Protective and Taste-Masking Coatings and Extended-Release Matrix Tablets.Drug Dev. Ind. Pharm. 29:925.
Royalty, et al. (2014) Investigation of safety, tolerability, pharmacokinetics, and pharmacodynamics of single and multiple doses of a long-acting alpha-MSH analog in healthy overweight and obese subjects. J Clin Pharmacol54(4):394-404.
Schmidt, et al., (2001) A multiparticulate drug-delivery system based on pellets incorporated into congealable olyethylene glycol carrier materials. Int. J. Pharm. 216:9.
Sebag, et al. (2013) Developmental control of the melanocortin-4 receptor by MRAP2 proteins in zebrafish. Science 341(6143):278-281.
Southern, et al. (2013) Screening beta-arrestin recruitment for the identification of natural ligands for orphan G-protein-coupled receptors. J Biomol Screening 18(5):599-609.
Srisai, et al. (2011) Characterization of the Hyperphagic Response to Dietary Fat in the MC4R Knockout Mouse. Endocrinology 152(3):890-902.
Tian, et al. (2014) Beta-arrestins and Gprotein-coupled receptor trafficking. Handbook of Experimental Pharmacology 219:173-186.
Zhang, et al. (2012) AgRP and POMC Neurons Are Hypophysiotropic and Coordinately Regulate multiple endocrine axes in a larval teleost. Cell Metab 15:256-264.

\* cited by examiner

POSITIVE ALLOSTERIC MODULATORS OF HUMAN MELANOCORTIN-4 RECEPTOR

CROSS REFERENCE TO RELATED APPLICATIONS

This application claims the benefit of priority to U.S. Provisional Application 62/346,892, filed Jun. 7, 2016, which is incorporated by reference herein in its entirety.

ACKNOWLEDGMENT OF GOVERNMENT SUPPORT

This invention was made with government support under Grant No. RO1 DK070332 awarded by the National Institutes of Health. The government has certain rights in the invention.

BACKGROUND

The melanocortin-4 receptor (MC4R) is a critical regulator of food intake and energy homeostasis (Cone R D (2005) Anatomy and regulation of the central melanocortin system. *Nature Neuroscience* 8(5):571-578). Furthermore, up to 5% of cases of severe pediatric obesity are due to heterozygosity for deleterious mutations in the MC4R gene (Farooqi I S, et al. (2003) Clinical spectrum of obesity and mutations in the melanocortin 4 receptor gene. *N Engl J Med* 348(12): 1085-1095).

Consequently, the MC4R has been considered a high priority target for the development of potent and selective orthosteric agonists for the treatment of obesity. Several groups have been successful at developing such compounds, including peptides and small molecules, and these molecules showed efficacy in significantly reducing weight in animal models from mice to primates (Kievit P, et al. (2012) Chronic treatment with a melanocortin-4 receptor agonist causes weight loss, reduces insulin resistance, and improves cardiovascular function in diet-induced obese rhesus macaques. *Diabetes* 62(2):490-497; Hess S, et al. (2008) Backbone cyclic peptidomimetic melanocortin-4 receptor agonist as a novel orally administered drug lead for treating obesity. *J Med Chem* 51(4):1026-1034; Joseph C G, et al. (2008) The 1,4-benzodiazepine-2,5-dione small molecule template results in melanocortin receptor agonists with nanomolar potencies. *J Med Chem* 51(5):1423-1431.

Unfortunately, most MC4R agonists tested caused an unacceptable target-mediated pressor effect that caused the termination of the trials (Greenfield J R, et al. (2009) Modulation of blood pressure by central melanocortinergic pathways. *N Engl J Med* 360(1):44-52). Because the MC4R is a critical regulator of energy homeostasis, it remains a very valuable target for the treatment of obesity, assuming molecules could be developed that segregate the weight loss and pressor activities. Indeed, two recently described peptide analogues of the endogenous MC4R ligand, α-melanocyte-stimulating hormone (α-MSH), NN2-0453 and RM493, cause weight loss in the absence of pressor activity, demonstrating the feasibility of separating these two MC4R-mediated activities (Royalty J E, Id.; Kievit P, Id.; Fosgerau K, et al. (2014) Novel alpha-MSH analog causes weight loss in obese rats and minipigs and improves insulin sensitivity. *J Endocrinol* 220(2):97-107).

In vivo, the activity of the MC4R is regulated by multiple endogenous ligands, including the agonists α, β, and γ-MSH, along with agouti-related protein, (AgRP). It is also regulated by multiple accessory proteins, including attractin-like protein (Haqq A M, et al. (2003) Characterization of a novel binding partner of the melanocortin-4 receptor: attractin-like protein. *Biochem J* 376(Pt 3):595-605), and MRAP2 (Asai M, et al. (2013) Loss of function of the melanocortin 2 receptor accessory protein 2 is associated with mammalian obesity. *Science* 341(6143):275-278; Josep-Agulleiro M, et al. (2013) Melanocortin 4 receptor becomes an ACTH receptor by coexpression of melanocortin receptor accessory protein 2. *Mol Endocrinol* 27(11): 1934-1945; Sebag J A, et al. (2013) Developmental control of the melanocortin-4 receptor by MRAP2 proteins in zebrafish. *Science* 341 (6143):278-281). In the case of most GPCRs, including other melanocortin receptors, loss of function mutations in one of the two alleles typically produces little to no phenotypic effect, perhaps due to the existence of spare receptors (Asano T, et al. (1984) Reconstitution of catecholamine-stimulated binding of guanosine 5'-O-(3-thiotriphosphate) to the stimulatory GTP-binding protein of adenylate cyclase. *Biochemistry* 23(23):5460-5467). In the case of many GPCRs, only a fraction of the receptors present need to be occupied by ligand to cause a full signaling and physiological effect. In contrast, the MC4R displays a gene-dosage effect, and haploinsufficiency in patients (Cody J D, et al. (1999) Haploinsufficiency of the melancortin-4 receptor gene in individuals with deletions of 18q. *Hum Genet* 105(5): 424-427) or mice (Huszar D, et al. (1997) Targeted disruption of the melanocortin-4 receptor results in obesity in mice. *Cell* 88:131-141) causes a morbid obesity syndrome with intermediate severity between the wild type and homozygous null individuals. MC4R haploinsufficiency causes intermediate effects on nearly all phenotypes measured, including food intake, body weight, linear growth, and autonomic outflow (Huszar D, Id.; Butler A A, et al. (2001) Melanocortin-4 receptor is required for acute homeostatic responses to increased dietary fat. *Nature Neuroscience* 4(6):605-611; Srisai D, et al. (2011) Characterization of the Hyperphagic Response to Dietary Fat in the MC4R Knockout Mouse. *Endocrinology* 152(3):890-902; da Silva A A, et al. (2008) Endogenous melanocortin system activity contributes to the elevated arterial pressure in spontaneously hypertensive rats. *Hypertension* 51(4):884-890). This rheostat-like property of the MC4R suggests that modest increases in MC4R signaling caused by a pharmaceutical agent could have beneficial outcomes on the obesity syndrome of MC4R haploinsufficient patients, and can even be useful in common obesity. What are thus needed are positive allosteric modulators (PAM) of MC4R and uses thereof to provide controlled potentiation of MC4R that respects the spatiotemporal characteristics of the activation of the receptor. Also needed are new methods of treating obesity, especially methods that do not induce the unwanted pressor effect. Still further, there is a need for molecules that can modulate MC4R signaling while allowing the retention of both the spatiotemporal characteristics and the regulation of this pathway by negative feedback loops and AgRP. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to compounds of Formula I:

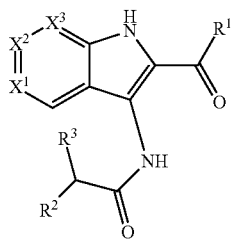

wherein
R[1] is $C_{1-8}$ alkyl, $C_{1-8}$ alkoxyl, $C_{3-7}$ cycloalkyl, $C_{2-8}$ alkenyl, $C_{5-6}$ cycloheteroalkenyl, $C_{2-8}$ alkynyl, any of which are optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol;

R[2] is $C_{5-6}$ cycloalkyl, $C_{5-6}$ cycloheteroalkyl, $C_{5-6}$ cycloalkenyl, $C_{5-6}$ cycloheteroalkenyl, phenyl, or heteroaryl, any of which are optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol;

R[3] is H or $C_{1-8}$ alkyl;

X[1], X[2], and X[3] are independently selected from N or CR[4]; and

R[4] is H, $C_{1-8}$ alkyl, $C_{1-8}$ alkoxyl, $C_{5-6}$ cycloheteroalkyl, carboxylic acid, ester, amino, halide, hydroxyl, nitro, $C_{1-8}$ alkylsulfonyl, $C_{5-6}$ arylsulfonyl, or thiol, or a pharmaceutically acceptable salt thereof.

Compounds of Formulas, II-A, II-B, II-C, II-D, and III are also disclosed, as are formulations and compositions comprising these compounds.

The disclosed compounds can be positive allosteric modulators of hMC4R. Further, the disclosed compounds can enhance the efficacy and potency of α-melanocyte-stimulating hormone to stimulate the Gαs signaling pathway.

In further aspects, disclosed are compositions that comprise compounds or compositions disclosed herein and a MC4R agonist or MC4R antagonist. In other aspects, disclosed are compositions that comprise compounds or compositions disclosed herein and α-, β-, or γ-melanocyte-stimulating hormone. Additional compositions are also disclosed such as a composition that comprises compounds or compositions disclosed herein and a compound that delays the progression from IGT to type 2 diabetes, delays the progression from type 2 diabetes to insulin-requiring diabetes, regulates appetite, induces satiety, prevents weight regain after successfully having lost weight, increases energy expenditure, treats erectile dysfunction, an antidiabetic agent, an antihyperlipidemic agent, an antiobesity agent, an antihypertensive agent, or an agent for the treatment of complications resulting from, or associated with, diabetes. Pharmaceutical compositions that comprise the compounds or compositions disclosed herein and a pharmaceutically acceptable carrier, are also disclosed.

In further aspects, disclosed are methods of modulating a melanocortin receptor (e.g., MC4R) that comprise administering to a subject in need thereof an effective amount of a compound or composition disclosed herein.

In further aspects, disclosed are methods of delaying the progression from impaired glucose tolerance to type 2 diabetes, or delaying the progression from type 2 diabetes to insulin-requiring diabetes that comprise administering to a subject in need thereof an effective amount of a compound or composition disclosed herein.

In further aspects, disclosed are methods of treating obesity, preventing overweight, regulating appetite, inducing satiety, or preventing weight regain after successfully having lost weight that comprise administering to a subject in need thereof an effective amount of a compound a compound or composition disclosed herein. Additional methods involving administering to a subject a compound or composition discloses herein are also described.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 1A is schematic representation of the cAMP traces obtained during a pGLO cAMP assay used for the identification of MC4R PAMs. FIG. 1B shows actual cAMP traces obtained from MC4R-Glo cells treated with α-MSH Emax (black), DMSO followed by α-MSH $EC_{20}$ (blue) or PAM followed by α-MSH $EC_{20}$. FIG. 1C shows actual cAMP traces obtained from the counterscreen using β2ADR-Glo cells treated with Isop Emax (black), DMSO followed by Isop $EC_{20}$ (blue) or MC4R PAM followed by Isop $EC_{20}$. FIG. 1D is a table containing the results of the primary screen and counterscreen.

FIGS. 2A, 2B, and 2C show structures of Examples 1-3, and the affect of Examples 1-3 on the α-MSH dose-response curve at the hMC4R, as determined using the Lance assay. Insets show the concentration-response effect as a function of the fold shift on the α-MSH concentration response curve. FIG. 2D shows a representative α-MSH (300 nM) inhibition of VIP-elevated Isc (short circuit current) in mouse colon mucosa in the absence (upper trace) or presence (lower trace) of Example 3 (1 µM; all additions were basolateral), in a Ussing chamber assay of ion flux across a mouse colonic mucosal sample. After α-MSH responses had waned all tissues received PYY (10 nM) to verify residual Y receptor anti-secretory activity. Basal Isc values are indicated to the left of each trace from an exposed area of 0.14 cm[2]. Vertical arrows show the timepoint at which α-MSH Isc responses were recorded. FIG. 2E shows that Example 3 alone (at 200 nM or 1 µM) on baseline Isc were not significantly different from vehicle (DMSO at 0.1%, the vehicle for 1 µM example 3). FIG. 2F shows that subsequent α-MSH responses were significantly increased by 1 µM example 3 pretreatment compared with vehicle controls. FIG. 2G shows that PYY responses were unaffected by Example 3 treatment (at 200 nM or 1 µM). FIG. 2H shows that α-MSH (300 nM) inhibition of Isc was significantly potentiated by 1 µM Example 3 and these responses were abolished by MC4R antagonist HS014 (30 nM) or by a combination of Y1 and Y2 receptor antagonists (+BIBO & BIIE; 300 nM BIBO3304 plus 1 µM BIIE0246). FIG. 2I shows that PYY responses (10 nM) were insensitive to HS014 but were predictably abolished by Y1 and Y2 receptor blockade. Each value is the mean±1 SEM with n values in parentheses. ** $P<0.01$ using one-way ANOVA with Dunnett's post-test.

FIG. 3C shows that subsequent α-MSH responses (300 nM) were potentiated significantly by pre-treatment with 3 µM Example 2, and (FIG. 3D) 10 µM Example 1. FIG. 3E shows that PYY (10 nM) responses were unaffected by Example 2 or (FIG. 3F) Example 1 pre-treatments. Each value is the mean±1 SEM with n values in parentheses. * $P<0.05$, ** $P<0.01$ using one-way ANOVA with Dunnett's post-test.

DETAILED DESCRIPTION

Figures 1A, 1B, 1C, 1D:
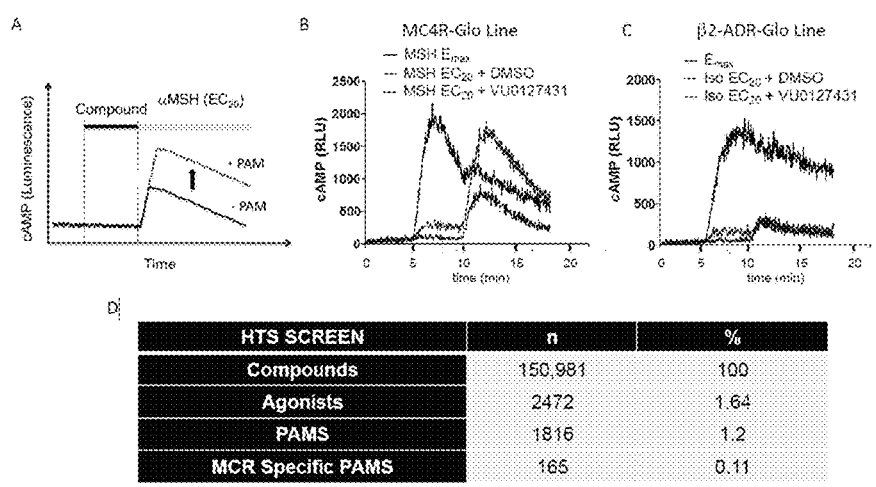
FIGS. 1A-1D contain results from high throughput screening.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings: Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., obesity). It is understood that this is typically in relation to some standard or expected value, in other words it is relative, but that it is not always necessary for the standard or relative value to be referred to. For example, "reduces obesity" means reducing the weight of a subject to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., obesity). The term "control" is used synonymously with the term "treat."

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "agonist" is intended to indicate a substance (ligand) that activates the receptor type in question. The term "agonist" includes full agonists as well as partial agonists.

The term "antagonist" is intended to indicate a substance (ligand) that blocks, neutralizes or counteracts the effect of an agonist. As used herein the term "antagonist" includes neutral antagonists and partial antagonists, as well as inverse agonists.

More specifically, receptor ligands may be classified as follows:

Receptor agonists, which activate the receptor; partial agonists also activate the receptor, but with lower efficacy than full agonists. A partial agonist will behave as a receptor partial antagonist, partially inhibiting the effect of a full agonist.

Receptor neutral antagonists, which block the action of an agonist, but do not affect the receptor-constitutive activity.

Receptor inverse agonists, which block the action of an agonist and at the same time attenuate the receptor-constitutive activity. A full inverse agonist will attenuate the receptor-constitutive activity completely; a partial inverse agonist will attenuate the receptor-constitutive activity to a lesser extent.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxyl, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxyl, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxyl, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxyl, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms, and typically less than 10. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. Examples of heterocycloalkyls are aziridine, oxirane, thiirane, diaziridine, oxaziridine, dioxirane, azetidine, oxetane, thietane, diazetidine, dioxetane, dithietane, pyrrolidine, tetrahydrofuran, tholane, phospholane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, and dithiane. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxyl, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. Examples of heterocycloakenyls are azirine, oxirene, thiirene, diazirine, zete oxete thiete, diazete, dioxete, dithiete, pyrrole, furan, thiophene, imidazole, pyrazole, oxazole, isoxazle, thiazole, isothiazole, triazole, furazan, oxadiazole, diathiazole, pyridine, pyran, thiopyran, diazine, oxazine, thiazine, dioxine, dithiine, and triazine. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxyl, ketone, nitro, silyl, sulfo-oxo, sulfonyl, sulfone, sulfoxide, or thiol as described herein.

The term "aldehyde" as used herein is represented by the formula —C(O)H. Throughout this specification "C(O)" or "CO" is a short hand notation for C=O, which is also referred to herein as a "carbonyl."

The terms "amine" or "amino" as used herein are represented by the formula —$NZ^1Z^2$, where $Z^1$ and $Z^2$ can each be a substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —$C(O)NZ^1Z^2$.

The term "carboxylic acid" as used herein is represented by the formula —C(O)OH. A "carboxylate" or "carboxyl" group as used herein is represented by the formula —C(O)O⁻;

The term "ester" as used herein is represented by the formula —$OC(O)Z^1$ or —$C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —$SiZ^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Positive allosteric modulators of GPCRs can enhance signaling by modifying different pharmacological properties of receptors (for review, see Christopoulos A (2014) Advances in G protein-coupled receptor allostery: from function to structure. *Mol Pharmacol* 86(5):463-478). They can increase the potency, the efficacy, or both, and even exhibit dual PAM and agonist activity even though binding to a site distinct from the orthosteric site (non-competitive Ago-PAMs). Many PAMs have been shown to increase the binding affinity of the endogenous agonist (Davey A E, et al. (2012) Positive and negative allosteric modulators promote biased signaling at the calcium-sensing receptor. *Endocrinol* 153(3):1232-1241), while others may lower the energy barrier for receptors to assume an active conformation. Specific synergism with ligand binding may explain the common observation of ligand or "probe" dependence of GPCR PAMs. Disclosed herein are the first small molecule PAMS of the hMC4R. PAMS were identified with a variety of chemotypes, and varying degrees of melanocortin receptor subtype specificity. Interestingly, none of the PAMs characterized altered affinity for the endogenous ligand, α-MSH, or exhibited probe dependence.

In specific examples, disclosed herein are compounds having Formula I:

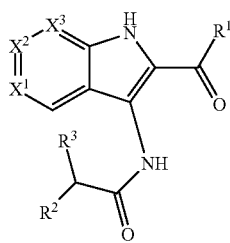

wherein
$R^1$ is $C_{1-8}$ alkyl, $C_{1-8}$ alkoxyl, $C_{3-7}$ cycloalkyl, $C_{2-8}$ alkenyl, $C_{5-6}$ cycloheteroalkenyl, $C_{2-8}$ alkynyl, any of which are optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol;
$R^2$ is $C_{5-6}$ cycloalkyl, $C_{5-6}$ cycloheteroalkyl, $C_{5-6}$ cycloalkenyl, $C_{5-6}$ cycloheteroalkenyl, phenyl, or heteroaryl, any of which are optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol;
$R^3$ is H or $C_{1-8}$ alkyl;
$X^1$, $X^2$, and $X^3$ are independently selected from N or $CR^4$; and
$R^4$ is H, $C_{1-8}$ alkyl, $C_{1-8}$ alkoxyl, $C_{5-6}$ cycloheteroalkyl, carboxylic acid, ester, amino, halide, hydroxyl, nitro, $C_{1-8}$ alkylsulfonyl, $C_{5-6}$ arylsulfonyl, or thiol,
or a pharmaceutically acceptable salt thereof.

In specific examples of Formula I, $R^1$ can be a $C_{3-8}$ cycloalkyl, for example, a cyclopropyl, cyclobutyl, cyclopentyl, cyclohexyl, or cycloheptyl. In even more specific example, $R^1$ can be cyclopropyl or cyclobutyl. In other examples, $R^1$ can be a $C_{1-4}$ alkoxyl, for example, a methoxyl, ethoxyl, propoxyl, or butoxyl. In still other examples, $R^1$ can be a $C_{1-8}$ alkyl, for example, methyl, ethyl, propyl, butyl, pentyl, hexyl, heptyl, or octyl. In more specific examples, $R^1$ can be methyl or ethyl. Any of these $R^1$ substituents can be optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol.

In other examples of Formula I, $R^2$ can be a $C_{5-6}$ cycloalkyl, for example cyclopentyl or cyclohexyl, or a $C_{5-6}$ cycloheteroalkyl, for example piperidinyl, piperazinyl, or morphilino, optionally substituted with one or more alkyl, alkoxy, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol. In specific examples, $R^2$ is a $C_{5-6}$ cycloalkyl or $C_{5-6}$ cycloheteroalkyl substituted with $C_{1-8}$ alkyl, $C_{1-8}$ alkoxyl, $C_{3-7}$ cycloalkyl, $OC_{5-6}$ cycloalkyl, phenyl, $N(C_{2-8}$ alkenyl)phenyl, NHphenyl, Ophenyl, heteroaryl, $N(C_{2-8}$ alkenyl)heteroaryl, NHheteroaryl, Oheteroaryl, or benzyl, any of which is optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol. In other examples $R^2$ is a $C_{5-6}$ cycloalkyl or $C_{5-6}$ cycloheteroalkyl substituted $C_{1-8}$ alkenyl or $C_{3-8}$ spiro-cycloalkyl, optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol.

In further examples of Formula I, $R^3$ can be H or methyl, ethyl, propyl, butyl, pentyl, hexyl, heptyl, or octyl. In more specific examples, $R^3$ can be methyl or ethyl. In many examples herein, $R^3$ is H.

In further examples of Formula I, $R^4$ can be H. In still other examples, $R^4$ can be halide, such as Cl or Br. In still other examples, $R^4$ can be $C_{1-4}$ alkyl, such as methyl, ethyl, propyl, or butyl. In yet further examples, $R^4$ can be methylsulfonyl, ethylsulfonyl, butylsulfonyl (e.g., t-butyl or sec-butylsulfonyl), or toluylsulfonyl. In still further examples, $R^4$ can be $C_6$ cycloheteroalkyl such as a piperidinyl, piperazinyl, or morpholino, any of which can be optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol. In still other examples, $R^4$ can be an amino group, such as $NH_2$, $NH(C_{1-8}$ alkyl), and $N(C_{1-8}$ alkyl)$_2$.

In further examples of Formula I, $X^1$, $X^2$, and $X^3$ can all CH. In other Examples, $X^1$ can be N, and $X^2$ and $X^3$ can be $CR^4$, where each $R^4$ can be independently selected from H, $C_{1-8}$ alkyl, $C_{1-8}$ alkoxyl, $C_{5-6}$ cycloheteroalkyl, carboxylic acid, ester, amino, halide, hydroxyl, nitro, $C_{1-8}$ alkylsulfonyl, $C_{5-6}$ arylsulfonyl, or thiol. In other examples, $X^2$ can be N and $X^1$ and $X^3$ can be $CR^4$, where each $R^4$ can be independently selected from H, $C_{1-8}$ alkyl, $C_{1-8}$ alkoxyl, $C_{5-6}$ cycloheteroalkyl, carboxylic acid, ester, amino, halide, hydroxyl, nitro, $C_{1-8}$ alkylsulfonyl, $C_{5-6}$ arylsulfonyl, or thiol. In still further examples, $X^3$ can be N and $X^1$ and $X^2$ can be $CR^4$, where each $R^4$ can be independently selected from H, $C_{1-8}$ alkyl, $C_{1-8}$ alkoxyl, $C_{5-6}$ cycloheteroalkyl, carboxylic acid, ester, amino, halide, hydroxyl, nitro, $C_{1-8}$ alkylsulfonyl, $C_{5-6}$ arylsulfonyl, or thiol. In further examples, $X^1$ can be $CR^4$, where $R^4$ is chosen from $C_{1-8}$ alkyl, $C_{1-8}$ alkoxyl, $C_{5-6}$ cycloheteroalkyl, carboxylic acid, ester, amino, halide, hydroxyl, nitro, $C_{1-8}$ alkylsulfonyl, $C_{5-6}$ arylsulfonyl, or thiol, and $X^2$ and $X^3$ can be CH. In further examples, $X^2$ can be $CR^4$, where $R^4$ is chosen from $C_{1-8}$ alkyl, $C_{1-8}$ alkoxyl, $C_{5-6}$ cycloheteroalkyl, carboxylic acid, ester, amino, halide, hydroxyl, nitro, $C_{1-8}$ alkylsulfonyl, $C_{5-6}$ arylsulfonyl, or thiol, and $X^1$ and $X^2$ can be CH.

Disclosed herein are compounds having Formula II-A and II-B:

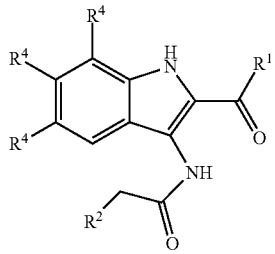

II-A

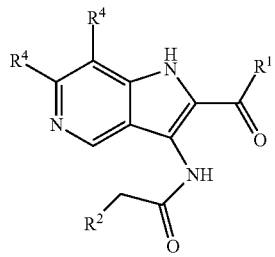

II-B

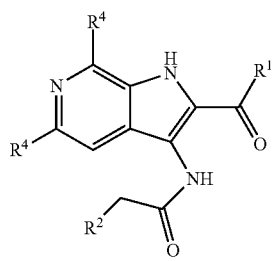

II-C

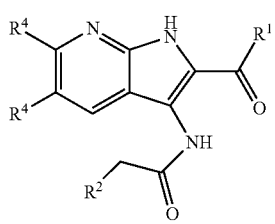

II-D wherein $R^1$, $R^2$, and $R^4$ are as described above in Formula I, and pharmaceutically acceptable salts thereof. In specific examples of Formula II-A and II-B, one $R^4$ is Br or Cl and the other $R^4$'s are H. In further examples, $R^1$ is methyl, ethyl, methoxyl, cyclopropyl, or cyclobutyl. In specific examples of Formula II-B, II-C, and II-D, where one $R^4$ is H and the other $R^4$ is Br or Cl. In other examples, where one $R^4$ is H and the other $R^4$ is methyl or methylsulfonyl. In still other examples, where one $R^4$ is H and the other $R^4$ is morpholino, any of which can be optionally substituted with one or more alkyl, alkoxy, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol.

In still further examples, disclosed herein are compounds having Formula III (which corresponds to Formula I where $R^2$ is an optionally substituted $C_{5-6}$ cycloheteroalkyl):

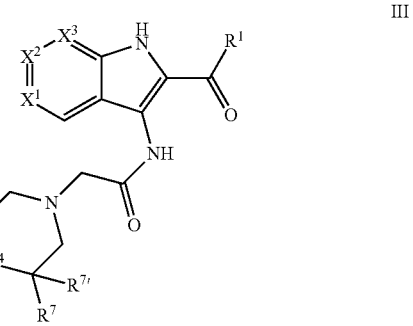

III wherein $R^1$, $X^1$, $X^2$, and $X^3$, are as described above in Formula I;

$X^4$ is $N(R^6)$, $C(R^6)(R^{6'})$, S, or O;

$R^6$ is H or $C_{1-8}$ alkyl, $C_{1-8}$ alkoxyl, $C_{3-7}$ cycloalkyl, $OC_{5-6}$ cycloalkyl, phenyl, $N(C_{2-8}$ alkenyl)phenyl, NHphenyl, Ophenyl, heteroaryl, $N(C_{2-8}$ alkenyl)heteroaryl, NHheteroaryl, Oheteroaryl, or benzyl, any of which is optionally substituted with one or more alkyl, alkoxy, haloalkyl, alkenyl, alkynyl, aryl, heteroaryl, aldehyde, amino, carboxylic acid, ester, ether, halide, hydroxyl, ketone, nitro, silyl, sulfonyl, sulfone, sulfoxide, or thiol; and $R^{6'}$ is H; or $R^6$ and $R^{6'}$ together forms $C_{1-8}$ alkenyl (e.g., methylene or isopropylene) or $C_{4-6}$ spiroalkyl; and $R^7$ and $R^{7'}$ are independently chosen from H and methyl, or pharmaceutically acceptable salts thereof.

In specific examples of Formula III, $R^6$ can be a $C_{1-4}$ alkyl, such as methyl, ethyl, propyl, or butyl (e.g., t-butyl). In other examples, $R^6$ can be a cyclohexyl. In other examples, $R^6$ can be $C_{3-7}$ cycloalkyl, such as cyclopropyl, cyclopentyl, and cyclohexyl. In further examples, $R^6$ can be phenyl, pyridinyl, indolyl, or benzyl, optionally substituted with one or more of $C_{1-4}$ alkyl, $C_{1-4}$ haloalkyl, $C_{1-4}$ alkoxyl, or halide.

In specific examples, $X^4$ is $N(R^6)$ and $R^6$ is phenyl or benzyl, optionally substituted with one or more of $C_{1-4}$ alkyl, $C_{1-4}$ haloalkyl, $C_{1-4}$ alkoxyl, and halide. Other protecting groups can be used as $R^6$, for example $R^6$ can be methyl substituted with two phenyls (i.e., diphenylmethyl), cyclopentyl with two fused phenyl substituents (i.e., fluorenyl).

In specific examples, $X^4$ is $C(R^6)(R^{6'})$, $R^6$ is cyclohexyl and $R^{6'}$ is H. In specific examples, $X^4$ is $C(R^6)(R^{6'})$, and $R^6$ is phenyl or benzyl, optionally substituted with one or more of $C_{1-4}$ alkyl, $C_{1-4}$ haloalkyl, $C_{1-4}$ alkoxyl, and halide, and $R^{6'}$ is H.

In specific examples of Formula III, $R^7$ and $R^{7'}$ are both H. In other examples $R^7$ and $R^{7'}$ are both methyl.

In further specific examples of Formula III, $R^1$ is methyl, ethyl, methoxyl, cyclopropyl, or cyclobutyl. In still further examples, $X^2$ and $X^3$ are CH, and $X^1$ is CH or C-halide.

In specific examples of Formula III, $X^4$ is N. In other examples of Formula III, $X^4$ is CH.

Specific examples of compounds disclosed herein are shown in Table 1:
TABLE 1
| Example | Structure | MW | hMC4R PAM LANCE pEC50 Mean | hMC4R PAM LANCE Asym Max |
|---|---|---|---|---|
| 1 | 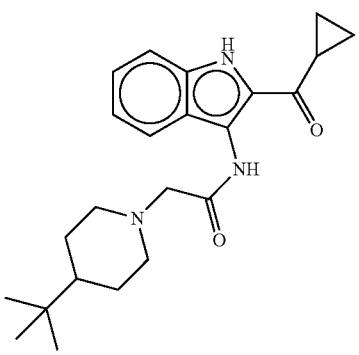 $C_{23}H_{31}N_3O_2$ | 381.51 | 6.2 | 86 |
| 2 | 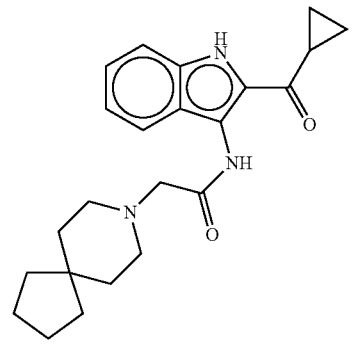 $C_{23}H_{29}N_3O_2$ | 379.5 | 6.3 | 81 |
| 3 | 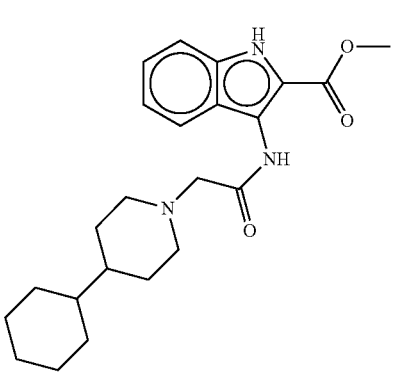 $C_{23}H_{31}N_3O_3$ | 397.51 | 6.7 | 99 |

TABLE 1-continued
| Example | Structure | MW | hMC4R PAM LANCE pEC50 Mean | hMC4R PAM LANCE Asym Max |
|---|---|---|---|---|
| 4 | 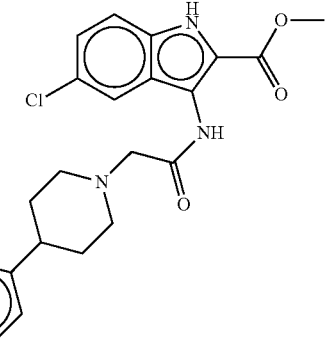 C₂₃H₂₄ClN₃O₃ | 425.91 | 6.5 | 90 |
| 5 | 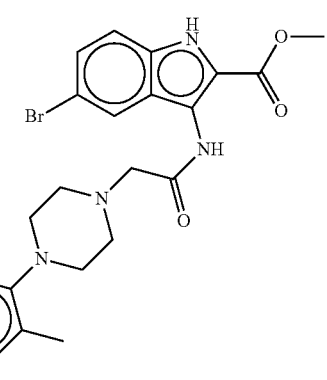 C₂₄H₂₇BrN₄O₃ | 499.4 | 6.5 | 78 |
| 6 | 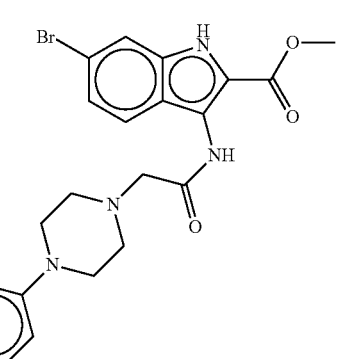 C₂₂H₂₂BrFN₄O₃ | 489.34 | 6.4 | 70 |

TABLE 1-continued
| Example | Structure | MW | hMC4R PAM LANCE pEC50 Mean | hMC4R PAM LANCE Asym Max |
|---|---|---|---|---|
| 7 | 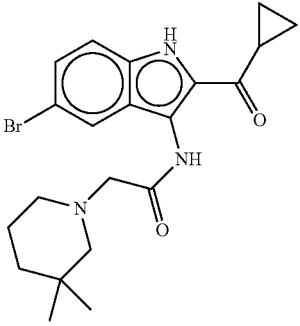 C21H26BrN3O2 | 432.35 | 6.4 | 58 |
| 8 | 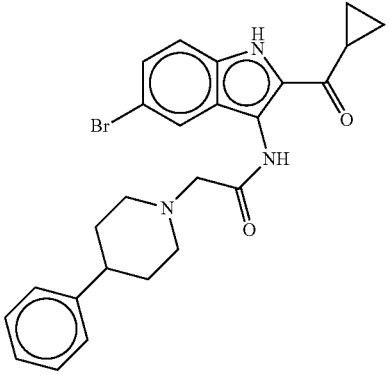 C25H26BrN3O2 | 480.4 | 6.5 | 58 |
| 9 | 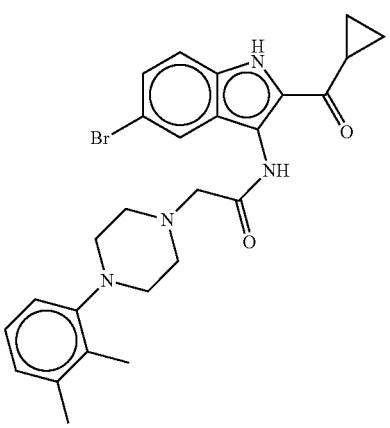 C26H29BrN4O2 | 509.44 | 6.4 | 68 |

TABLE 1-continued

| Example | Structure | MW | hMC4R PAM LANCE pEC50 Mean | hMC4R PAM LANCE Asym Max |
|---|---|---|---|---|
| 10 | C₂₆H₃₀N₄O₂ | 430.54 | 6.5 | 71 |
| 11 | C₂₃H₂₅N₃O₃ | 391.46 | 6.5 | 97 |
| 12 | C₂₃H₂₃F₃N₄O₃ | 460.45 | 6.3 | 69 |

TABLE 1-continued
| Example | Structure | MW | hMC4R PAM LANCE pEC50 Mean | hMC4R PAM LANCE Asym Max |
|---|---|---|---|---|
| 13 | 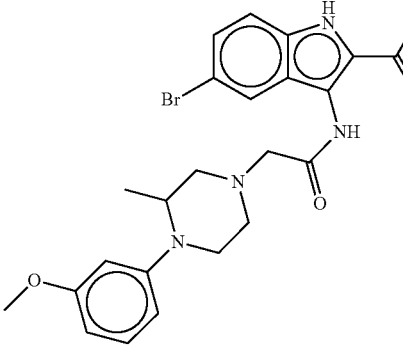 C24H27BrN4O4 | 515.4 | 6.3 | 68 |
| 14 | 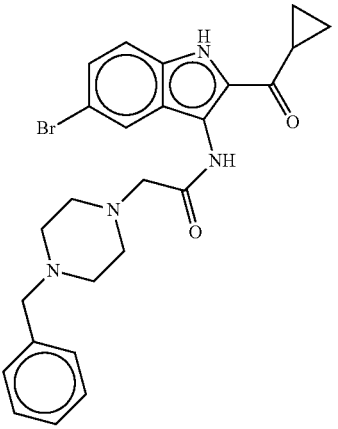 C25H27BrN4O2 | 495.41 | 6.2 | 30 |
| 15 | 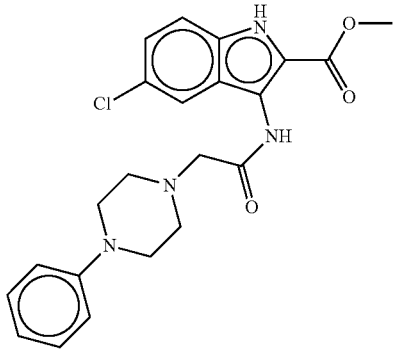 C22H23ClN4O3 | 426.9 | 6.2 | 78 |

TABLE 1-continued
| Example | Structure | MW | hMC4R PAM LANCE pEC50 Mean | hMC4R PAM LANCE Asym Max |
|---|---|---|---|---|
| 16 | 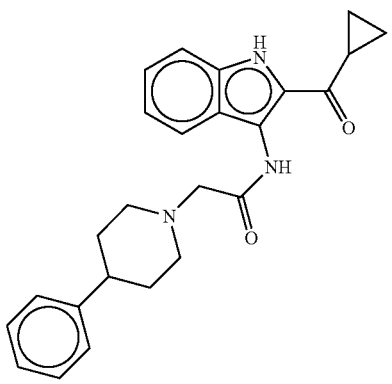<br>C25H27N3O2 | 401.5 | 6.2 | 57 |
| 17 | 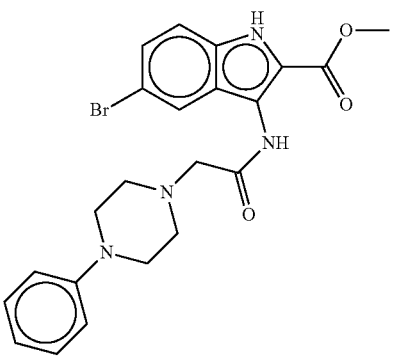<br>C22H23BrN4O3 | 471.35 | 6.2 | 70 |
| 18 | 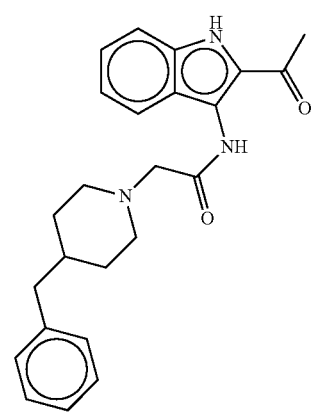<br>C24H27N3O2 | 389.49 | 6.1 | 65 |

TABLE 1-continued

| Example | Structure | MW | hMC4R PAM LANCE pEC50 Mean | hMC4R PAM LANCE Asym Max |
|---|---|---|---|---|
| 19 | C₂₃H₂₅N₃O₂ | 375.46 | 6.2 | 68 |
| 20 | C₂₅H₂₈BrN₃O₃ | 498.41 | 6.2 | 89 |
| 21 | C₂₄H₂₆ClN₃O₃ | 439.94 | 6.2 | 94 |

TABLE 1-continued

| Example | Structure | MW | hMC4R PAM LANCE pEC50 Mean | hMC4R PAM LANCE Asym Max |
|---------|-----------|-----|------|------|
| 22 | C₂₄H₂₆BrN₃O₃ | 484.39 | 6.2 | 87 |
| 23 | C₂₁H₂₇N₃O₂ | 353.46 | 6.1 | 63 |
| 24 | C₂₄H₂₇N₃O₃ | 405.49 | 6 | 97 |

TABLE 1-continued

| Example | Structure | MW | hMC4R PAM LANCE pEC50 Mean | hMC4R PAM LANCE Asym Max |
|---|---|---|---|---|
| 25 | C₂₃H₂₅N₃O₄ | 407.46 | 6 | 81 |
| 26 | C₁₇H₂₀BrN₃O₃ | 394.26 | 6 | 35 |
| 27 | C₂₅H₃₀N₄O₃ | 434.53 | 5.9 | 92 |
| 28 | C₁₉H₂₆N₄O₃ | 358.43 | 5.8 | 71 |

TABLE 1-continued

| Example | Structure | MW | hMC4R PAM LANCE pEC50 Mean | hMC4R PAM LANCE Asym Max |
|---|---|---|---|---|
| 29 | C₂₀H₂₅N₃O₃ | 355.43 | 5.9 | 93 |
| 30 | C₂₅H₂₉N₃O₃ | 419.52 | 5.9 | 96 |
| 31 | C₂₅H₃₀N₄O₄ | 450.53 | 5.8 | 73 |
| 32 | C₂₂H₂₄N₄O₄ | 408.45 | 5.8 | 82 |

TABLE 1-continued
| Example | Structure | MW | hMC4R PAM LANCE pEC50 Mean | hMC4R PAM LANCE Asym Max |
|---|---|---|---|---|
| 33 | 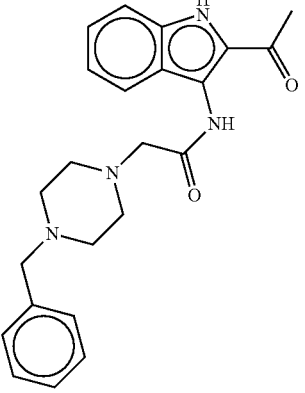<br>C₂₃H₂₆N₄O₂ | 390.48 | 5.6 | 29 |
| 34 | 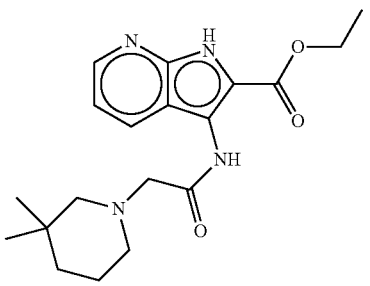<br>C₁₉H₂₆N₄O₃ | 358.43 | 5.7 | 25 |
| 35 | 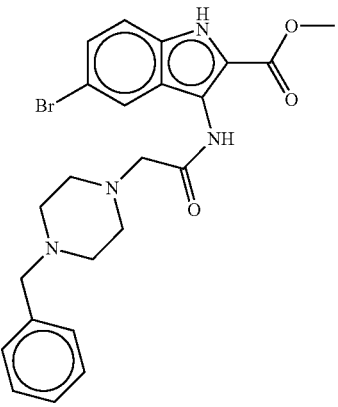<br>C₂₃H₂₅BrN₄O₃ | 485.37 | 5.8 | 66 |
| 36 | 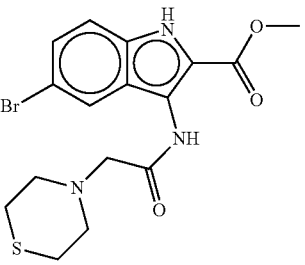<br>C₁₆H₁₈BrN₃O₃S | 412.3 | 5.8 | 46 |

TABLE 1-continued

| Example | Structure | MW | hMC4R PAM LANCE pEC50 Mean | hMC4R PAM LANCE Asym Max |
|---|---|---|---|---|
| 37 | C₂₅H₃₃N₃O₂ | 407.55 | 6.6 | 72 |
| 38 | C₂₅H₃₂ClN₃O₂ | 441.99 | 6.6 | 69 |
| 39 | C₂₃H₂₄BrN₃O₃ | 470.36 | 6.6 | 89 |

TABLE 1-continued
| Example | Structure | MW | hMC4R PAM LANCE pEC50 Mean | hMC4R PAM LANCE Asym Max |
|---|---|---|---|---|
| 40 | 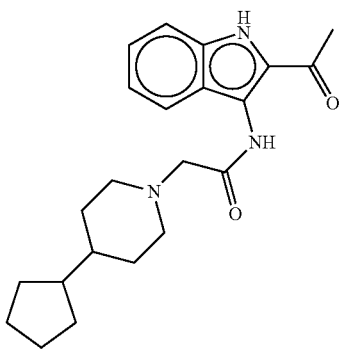 $C_{22}H_{29}N_3O_2$ | 367.48 | 6.5 | 78 |
| 41 | 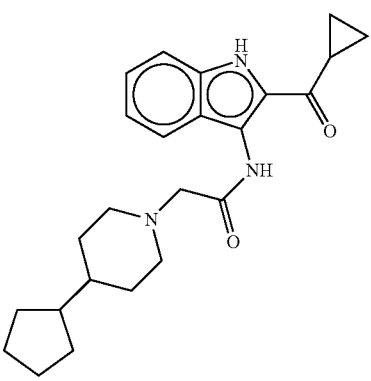 $C_{24}H_{31}N_3O_2$ | 393.52 | 6.4 | 72 |
| 42 | 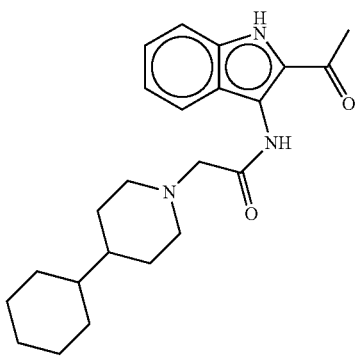 $C_{23}H_{31}N_3O_2$ | 381.51 | 6.5 | 73 |

TABLE 1-continued

| Example | Structure | MW | hMC4R PAM LANCE pEC50 Mean | hMC4R PAM LANCE Asym Max |
|---|---|---|---|---|
| 43 | C₂₃H₂₄BrN₃O₂ | 454.36 | 6.4 | 64 |
| 44 | C₂₄H₂₆BrN₃O₂ | 468.39 | 6.4 | 67 |
| 45 | C₂₄H₂₈N₄O₃ | 420.5 | 6.3 | 100 |

TABLE 1-continued

| Example | Structure | MW | hMC4R PAM LANCE pEC50 Mean | hMC4R PAM LANCE Asym Max |
|---|---|---|---|---|
| 46 | C₂₉H₂₇BrN₄O₃ | 559.45 | 6.3 | 48 |
| 47 | C₂₉H₂₉BrN₄O₃ | 561.47 | 6.2 | 61 |
| 48 | C₂₂H₂₉N₃O₄S | 431.55 | 6.3 | 53 |

TABLE 1-continued
| Example | Structure | MW | hMC4R PAM LANCE pEC50 Mean | hMC4R PAM LANCE Asym Max |
|---|---|---|---|---|
| 49 | 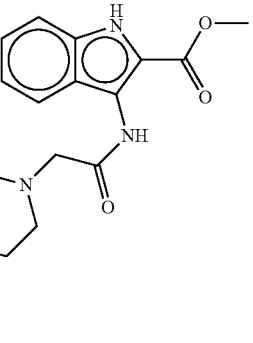 C25H28N4O3 | 432.51 | 6.2 | 89 |
| 50 | 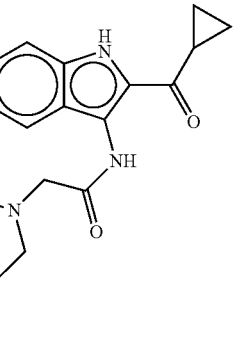 C22H27N3O2 | 365.47 | 6.1 | 58 |
| 51 | 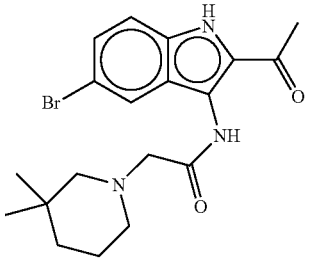 C19H24BrN3O2 | 406.32 | 6 | 51 |
| 52 | 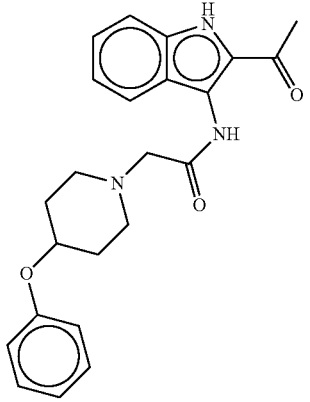 C23H25N3O3 | 391.46 | 5.9 | 57 |

TABLE 1-continued
| Example | Structure | MW | hMC4R PAM LANCE pEC50 Mean | hMC4R PAM LANCE Asym Max |
|---|---|---|---|---|
| 53 | 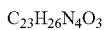 $C_{25}H_{34}N_4O_3$ | 438.56 | 5.7 | 51 |
| 54 | 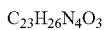 $C_{22}H_{27}N_3O_2$ | 365.47 | 6 | 73 |
| 55 | 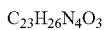 $C_{23}H_{26}N_4O_3$ | 406.48 | 5.8 | 72 |

TABLE 1-continued

| Example | Structure | MW | hMC4R PAM LANCE pEC50 Mean | hMC4R PAM LANCE Asym Max |
|---|---|---|---|---|
| 56 | C<sub>26</sub>H<sub>29</sub>N<sub>3</sub>O<sub>2</sub> | 415.53 | 5.9 | 21 |
| 57 | C<sub>25</sub>H<sub>30</sub>N<sub>4</sub>O<sub>3</sub> | 434.53 | 5.6 | 83 |
| 58 | C<sub>26</sub>H<sub>35</sub>N<sub>3</sub>O<sub>4</sub>S | 485.64 | 7.1 | 46 |

TABLE 1-continued
| Example | Structure | MW | hMC4R PAM LANCE pEC50 Mean | hMC4R PAM LANCE Asym Max |
|---|---|---|---|---|
| 59 | 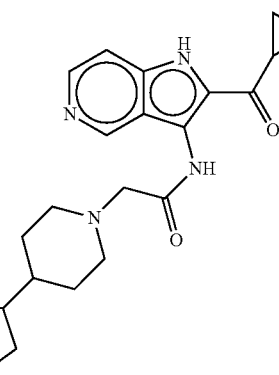 C₂₃H₃₀N₄O₂ | 394.51 | 6.7 | 54 |
| 60 | 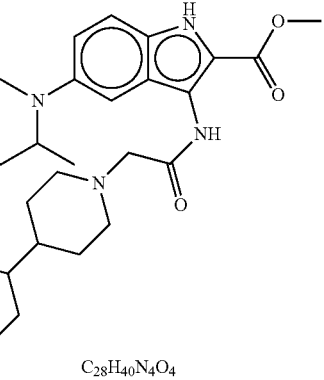 C₂₈H₄₀N₄O₄ | 496.64 | 6.7 | 88 |
| 61 | 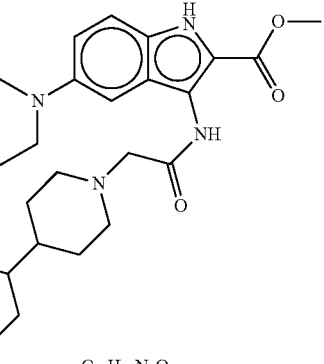 C₂₇H₃₈N₄O₄ | 482.62 | 6.6 | 96 |

TABLE 1-continued

| Example | Structure | MW | hMC4R PAM LANCE pEC50 Mean | hMC4R PAM LANCE Asym Max |
|---|---|---|---|---|
| 62 | C₂₄H₃₂N₄O₂ | 408.54 | 6.6 | 50 |
| 63 | C₂₄H₃₀ClN₃O₂ | 427.97 | 6.7 | 65 |
| 64 | C₂₁H₂₈N₄O₂ | 368.47 | 6.6 | 58 |

TABLE 1-continued
| Example | Structure | MW | hMC4R PAM LANCE pEC50 Mean | hMC4R PAM LANCE Asym Max |
|---|---|---|---|---|
| 65 | 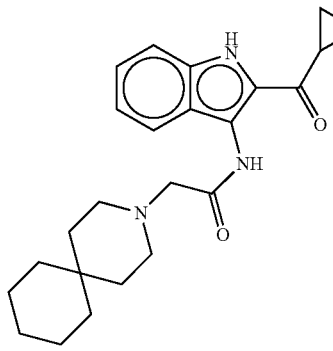 C₂₄H₃₁N₃O₂ | 393.52 | 6.5 | 83 |
| 66 | 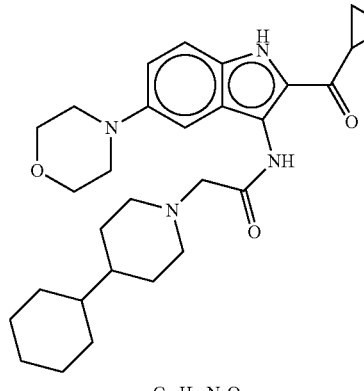 C₂₉H₄₀N₄O₃ | 492.65 | 6.6 | 59 |
| 67 | 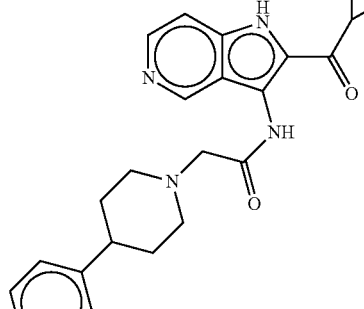 C₂₄H₂₆N₄O₂ | 402.49 | 6.5 | 47 |

TABLE 1-continued

| Example | Structure | MW | hMC4R PAM LANCE pEC50 Mean | hMC4R PAM LANCE Asym Max |
|---|---|---|---|---|
| 68 | C₂₂H₂₈N₄O₂ | 380.48 | 6.4 | 57 |
| 69 | C₂₉H₃₄N₄O₃ | 486.61 | 6.3 | 49 |
| 70 | C₂₃H₃₁N₃O₂ | 381.51 | 6.4 | 77 |

TABLE 1-continued
| Example | Structure | MW | hMC4R PAM LANCE pEC50 Mean | hMC4R PAM LANCE Asym Max |
|---|---|---|---|---|
| 71 | 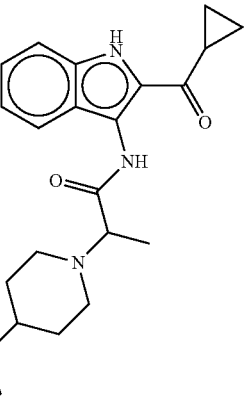 C25H33N3O2 | 407.55 | 6.4 | 75 |
| 72 | 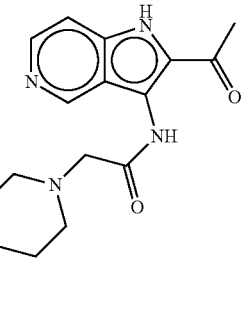 C20H28N4O2 | 356.46 | 6.3 | 57 |
| 73 | 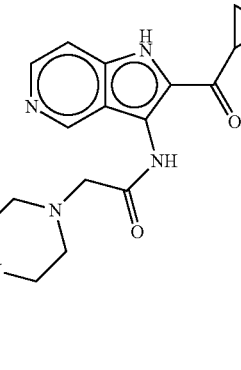 C23H25N5O2 | 403.48 | 6.2 | 47 |

TABLE 1-continued

| Example | Structure | MW | hMC4R PAM LANCE pEC50 Mean | hMC4R PAM LANCE Asym Max |
|---|---|---|---|---|
| 74 | C20H26N4O2 | 354.45 | 6.2 | 52 |
| 75 | C25H29N3O3 | 419.52 | 5.9 | 100 |
| 76 | C26H36N4O3 | 452.59 | 5.7 | 52 |
| 77 | C23H31N3O3 | 397.51 | 5.8 | 60 |

TABLE 1-continued
| Example | Structure | MW | hMC4R PAM LANCE pEC50 Mean | hMC4R PAM LANCE Asym Max |
|---|---|---|---|---|
| 78 | 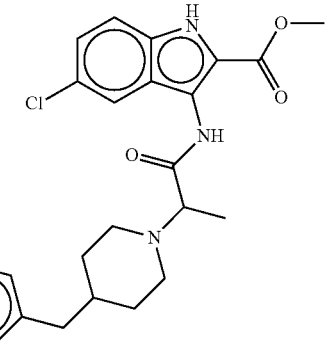 C25H28ClN3O3 | 453.96 | 6 | 95 |
| 79 | 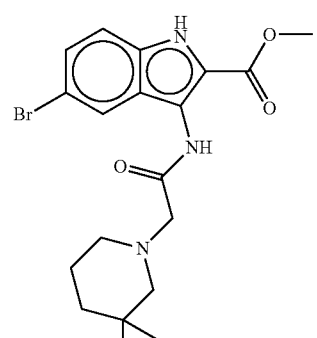 C19H24BrN3O3 | 422.32 | 6.1 | 84 |
| 80 | 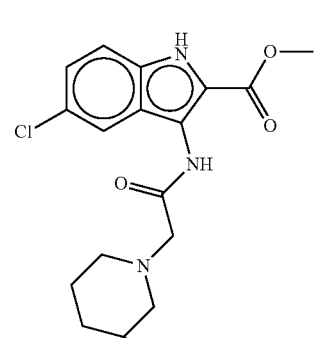 C19H24ClN3O3 | 377.87 | 6 | 93 |

In more specific examples, disclosed are compounds have the structure:

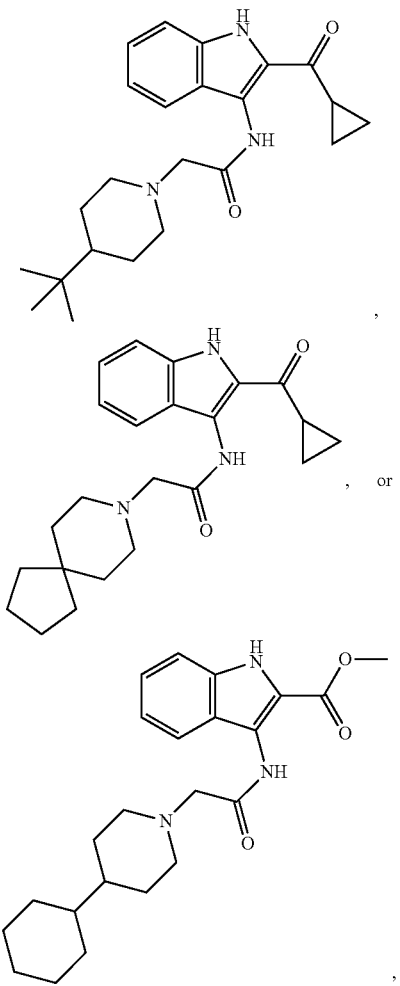

or pharmaceutically acceptable salts thereof.

Also disclosed herein are pharmaceutically acceptable salts of the disclosed compounds. Thus, contemplated herein are methods and compositions that have the compounds disclosed herein in the form of salts, including acid addition salts. Suitable salts include those formed with both organic and inorganic acids. Such acid addition salts will normally be pharmaceutically acceptable. However, salts of non-pharmaceutically acceptable salts can be of utility in the preparation and purification of the compound in question. Basic addition salts can also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "pharmaceutically acceptable salt," as used herein, represents salts or zwitterionic forms of the compounds disclosed herein which are water or oil-soluble or dispersible and pharmaceutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

Formulations

While it can be possible for compounds disclosed herein to be administered as the neat compound, it is also possible to present them as a pharmaceutical formulation.

Accordingly, provided herein are pharmaceutical formulations which comprise one or more of the disclosed compounds, or one or more pharmaceutically acceptable salts, esters, prodrugs, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients can be used as suitable and as understood in the art; e.g., in *Remington: The Science and Practice of Pharmacy*, 21$^{st}$ Ed., Gennaro, Ed., Lippencott Williams & Wilkins (2003). The pharmaceutical compositions disclosed herein can be manufactured in any manner known in the art, e.g., by means of conventional mixing, dissolving, granulating, dragee-making, levigating, emulsifying, encapsulating, entrapping or compression processes.

A compound as provided herein can be incorporated into a variety of formulations for therapeutic administration, including solid, semi-solid, liquid or gaseous forms. The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route can depend upon for example the condition and disorder of the recipient. The formulations can conveniently be presented in unit dosage form and can be prepared by any of the methods well known in the art of pharmacy. Typically, these methods include the step of bringing into association a compound or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders, inert diluents, or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt. For buccal or sublingual administration, the compositions can take the form of tablets, lozenges, pastilles, or gels formulated in conventional manner. Such compositions can comprise the active ingredient in a flavored basis such as sucrose and acacia or tragacanth. In one example, a compound is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The precise amount of compound administered to an individual will be the responsibility of the attendant physician. The specific dose level for any particular individual will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration can vary depending on the condition and its severity. The dosage can be increased or decreased over time, as required by an individual. An individual initially can be given a low dose, which is then increased to an efficacious dosage tolerable to the individual. Typically, a useful dosage for adults can be from 5 to 2000 mg, but have been known to range from 0.1 to 500 mg/kg per day. By way of example, a dose can range from 1 to 200 mg, when administered by oral route; or from 0.1 to 100 mg or, in certain embodiments, 1 to 30 mg, when administered by intravenous route; in each case administered, for example, from 1 to 4 times per day. When a compound is administered in combination with another therapeutic agent, a useful dosage of the combination partner can be from 20% to 100% of the normally recommended dose, since, as discussed below, even doses of a given drug which would be subtherapeutic if administered on its own can be therapeutic when used in combination with another agent.

Dosage amount and interval can be adjusted individually to provide plasma levels of the active compounds that are sufficient to maintain therapeutic effect. In certain examples, therapeutically effective serum levels will be achieved by administering single daily doses, but efficacious multiple daily dose schedules can be used as well. In cases of local administration or selective uptake, the effective local concentration of the drug cannot be related to plasma concentration. The skilled practitioner will be able to optimize therapeutically effective local dosages without undue experimentation. Additionally, applicable methods for determining an appropriate dose and dosing schedule for administration of compounds such as those disclosed herein are described, for example, in *Goodman and Gilman's The Pharmacological Basis of Therapeutics*, 11th Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

The compounds disclosed herein can also be combined with one or more additional therapeutically active compounds or substances. For example, the disclosed compounds can be admixed with compounds that delay the progression from IGT to type 2 diabetes, delay the progression from type 2 diabetes to insulin-requiring diabetes, regulate appetite, induce satiety, prevent weight regain after successfully having lost weight; or increase energy expenditure, agent that treats erectile dysfunction, antidiabetic agents, antihyperlipidemic agents, antiobesity agents, antihypertensive agents and agents for the treatment of complications resulting from, or associated with, diabetes. In another specific example, the disclosed compounds can be combined with MC4R agonists or antagonists. Specific examples of MC4R agonists are disclosed in WO 99/64002; WO 00/74679; WO 01/70708; WO 01/70337; and WO 01/91752, which are incorporated by reference herein for their teachings of MC4R agonists.

In another example the compounds disclosed herein can be combined with a α-, β-, or γ-melanocyte-stimulating hormone (α-MSH, β-MSH, and γ-MSH).

Methods

Since a 50% reduction in MC4R activity causes morbid obesity, MC4R PAMs can be used for the treatment of the melanocortin haploinsufficiency syndrome found in approximately 1/1500 individuals. A two-fold increase in MC4R signaling in vivo would have a dramatic effect on energy storage and body weight. Further, the more potent MC4R PAMs in the indole series show activity and specificity at the native MC4R of the mouse intestinal L cell that parallels data obtained from MC4R transfected cells, proving that allosteric modulators isolated in a spatiotemporal screening program can be utilized to improve activity of the native receptor in vivo. Studies show anorexigenic activity of Example 3 in vivo in the mouse.

hMC4R PAMs can be a safe alternative to potent orthosteric agonists of the MC4R for the treatment of common obesity because PAMs allow MC4R signaling to be amplified while retaining the normal physiological characteristics of the system. In addition, unlike orthosteric agonists, PAMs allow the organism to retain control of MC4R signaling through negative feedback regulation, since the activity of the receptor still depends on the secretion of the endogenous agonist. Recently, an endogenous allosteric modulator of the MC4R, the protein MRAP2, has been characterized (Sebag J A, et al. (2013) Developmental control of the melanocortin-4 receptor by MRAP2 proteins in zebrafish. *Science* 341(6143):278-281). Likewise, the MC4R has also been demonstrated to couple to an inward rectifier channel, Kir7.1, in a G protein-independent manner (Ghamari-Langroudi M, et al. (2015) G-protein-independent coupling of MC4R to Kir7.1 in hypothalamic neurons. *Nature* doi:10.1038/nature14051, 2015).

As such, compounds disclosed herein modulate melanocortin receptors, and they are therefore believed to be particularly suited for the treatment of diseases or states that can be treated by a modulation of melanocortin receptor activity. In particular, the disclosed compounds can be used for the treatment of diseases or states via modulation of MC4R.

In one aspect, disclosed herein is a method of modulating MC4R in a subject, the method comprising administering to the subject an effective amount of a compound disclosed herein (e.g., a compound of Formula I).

In another aspect, disclosed herein is a method of delaying the progression from impaired glucose tolerance (IGT) to type 2 diabetes, the method comprising administering to a subject in need thereof an effective amount of a compound disclosed herein.

In a further aspect, disclosed herein is a method of delaying the progression from type 2 diabetes to insulin-requiring diabetes, the method comprising administering to a subject in need thereof an effective amount of a compound disclosed herein. In an additional aspect, disclosed herein is a method of treating obesity or preventing overweight, the method comprising administering to a subject in need thereof an effective amount of a compound disclosed herein.

In a still further aspect, disclosed herein is a method of regulating appetite, the method comprising administering to a subject in need thereof an effective amount of a compound disclosed herein.

In yet another aspect, disclosed herein is a method of inducing satiety, the method comprising administering to a subject in need thereof an effective amount of a compound disclosed herein.

In a further aspect, disclosed herein is a method of preventing weight regain after successfully having lost weight, the method comprising administering to a subject in need thereof an effective amount of a compound disclosed herein.

In a still further aspect, disclosed herein is a method of increasing energy expenditure, the method comprising administering to a subject in need thereof an effective amount of a compound disclosed herein.

Still further aspects of the invention include the following:

a method of treating a disease or state related to overweight or obesity, the method comprising administering to a subject in need thereof an effective amount of a compound disclosed herein;

a method of treating bulimia, the method comprising administering to a subject in need thereof an effective amount of a compound disclosed herein;

a method of treating binge-eating, the method comprising administering to a subject in need thereof an effective amount of a compound disclosed herein;

a method of treating a disease or state selected from atherosclerosis, hypertension, diabetes, type 2 diabetes, impaired glucose tolerance (IGT), dyslipidemia, coronary heart disease, gallbladder disease, gall stone, osteoarthritis, cancer, sexual dysfunction and risk of premature death, the method comprising administering to a subject in need thereof an effective amount of a compound disclosed herein.

In particular, a compound disclosed herein can be suited for the treatment of diseases in obese or overweight subjects. Accordingly, disclosed herein is a method of treating, in an obese subject, a disease or state selected from type 2 diabetes, impaired glucose tolerance (IGT), dyslipidemia, coronary heart disease, gallbladder disease, gall stone, osteoarthritis, cancer, sexual dysfunction and risk of premature death in obese subjects, the method comprising administering to an obese subject in need thereof an effective amount of a compound disclosed herein.

Moreover, administration of compound disclosed herein can be advantageous in the treatment of subjects, notably obese or overweight subjects, who have undergone, or are to undergo, gastric banding and/or gastric surgery.

In addition, MC4 modulators could have a positive effect on insulin sensitivity, on drug abuse by modulating the reward system and on hemorrhagic shock. Furthermore, MC3 and MC4 agonists have antipyretic effects, and both have been suggested to be involved in peripheral nerve regeneration. MC4 agonists are also known to reduce stress response. Thus, the disclosed compounds can be administered with MC4 agonists.

In all of the therapeutic methods disclosed above, a compound disclosed herein can be administered alone or in combination with one or more (i.e. one or two or three . . . etc.) additional compounds disclosed herein. Moreover, a compound disclosed herein, or a combination of two or more (i.e. two or three or four . . . etc.) compounds disclosed herein, may be administered in combination with one or more other therapeutically active agents or compounds (e.g., MC4 agonists), either sequentially or concomitantly.

In still another method disclosed herein is a method of treating erectile dysfunction by administering to a subject in need thereof a compound as disclosed herein.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

pGLO Assay

Drug screening for identification of hits and initial characterization of MC4R PAM compounds were performed using the pGLO assay, as described previously (Pantel J, et al., (2011) Development of a high throughput screen for allosteric modulators of melanocortin-4 receptor signaling using a real time cAMP assay. *Eur J Pharmacol* 660:139-147. HEK293 cells stably expressing the hMC4R or the hB2ADR with GloSensor (Promega) were plated at a density of 10,000 to 15,000 cells per well on Poly-D-Lysin coated black optical bottom 384 well plates in MEM supplemented with 2% serum. The next day, cells were loaded with the cAMP Glo reagent at a 2% concentration in $CO_2$-independent media for 2 hours at 37° C. Assay was performed using the Hamamatsu FDSS 6000 following the protocol depicted in FIGS. 1A-1D. α-MSH was from Bachem (H-1075; Ac-Ser-Tyr-Ser-Met-Glu-His-Phe-Arg-Trp-Gly-Lys-Pro-Val-$NH_2$) (SEQ ID. NO.:1). Analysis and hit picking was performed by comparing each trace obtained to the closest control well on the plate.

LANCE Assay

Analysis of pharmacological properties of compounds was performed using the LANCE cAMP kit (Perkin Elmer). HEK293 cells stably expressing the hMC4R were treated with PAM compounds at doses indicated, then incubated with an Alexa Fluor 647-labeled antibody in stimulation buffer according to manufacturer's instructions for 30 min at RT. Next, α-MSH was added (at an $EC_{20}$ dose or at doses indicated for concentration-response curves), and plates were incubated for 15 minutes at RT, followed by the addition of 10 μL of detection mix. Plates were then incubated for 30 minutes at RT and read on a Viewlux (Perkin Elmer) using 618 and 671 nm emission filters. IBMX was not included in the assay.

Ussing Chamber Assay

GI tissue from adult (12-20 week old) male C57BL/6J mice were dissected free of overlying smooth muscle and mucosae placed between 2 halves of Ussing chambers exposing an area of 0.14 $cm^2$. Mucosae were bathed both sides with Krebs-Henseleit (KH) buffer of following composition (in mM: 117 NaCl, 24.8 $NaHCO_3$, 4.7 KCl, 1.2 $MgSO_4$, 1.2 $KH_2PO_4$, 2.5 $CaCl_2$ and 11.1 D-glucose) aerated with 95% $O_2$/5% $CO_2$ (pH 7.4) and voltage-clamped at 0 mV as described in detail previously (Cox et al., 2001; Cox and Tough, 2002). MC4R activity in mouse colonic epithelium was then characterized. Mouse mucosae were pre-treated with vehicle or PAM compounds, then with secret-agogue, VIP (10 nM, basolateral), and once elevated ISC had reached its peak and was declining at a constant rate, α-MSH was added to the basolateral reservoir to determine responses.

ISC responses in μA are expressed as the mean±SEM per unit area (cm2). Single comparisons (using GraphPad Prism) were performed using Student's unpaired t-test while multiple comparisons utilized 1-way ANOVA with Dunnett's post test and P≤0.05 were considered statistically significant.

Indole Series Design and Testing

Figures 2A, 2B, 2C, 2D, 2E, 2F, 2G, 2H, 2I:
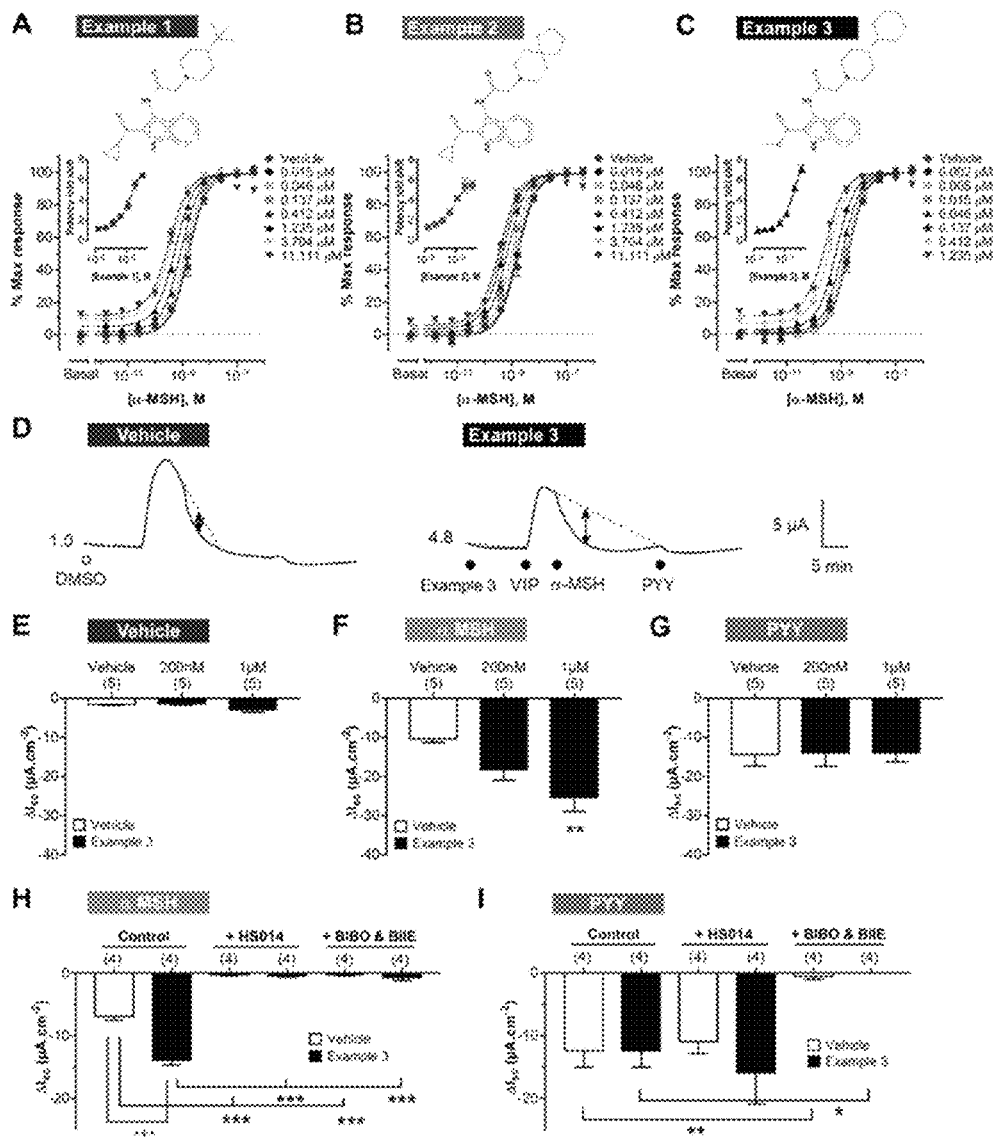
FIGS. 2A-2I contain data on the characterization of hMC4R PAMs Examples 1, 2, and 3.
Figures 3A, 3B, 3C, 3D, 3E, 3F:
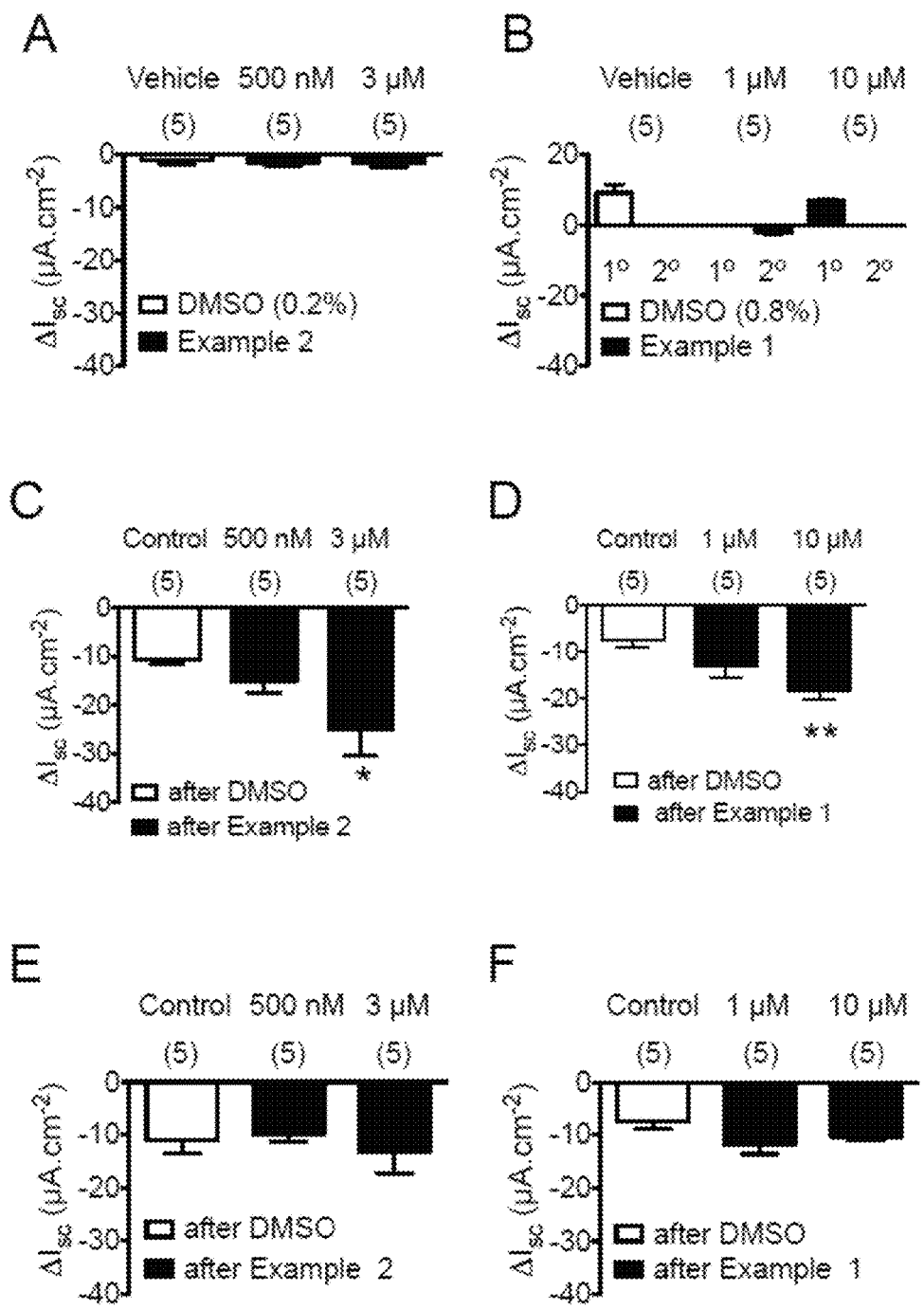
FIGS. 3A-3F contain data showing that the basolateral effects of Example 2 (FIG. 3A) and Example 1 (FIG. 3B) on basal Isc were not significantly different to vehicle controls. The vehicle (0.8% DMSO) required for 10 µM Example 1, induced an increase in Isc (1°) prior to slower reductions in Isc (2°). The 1° phase was not observed with the lower concentration of Example 1 (in 0.08% DMSO).
Figure 4:
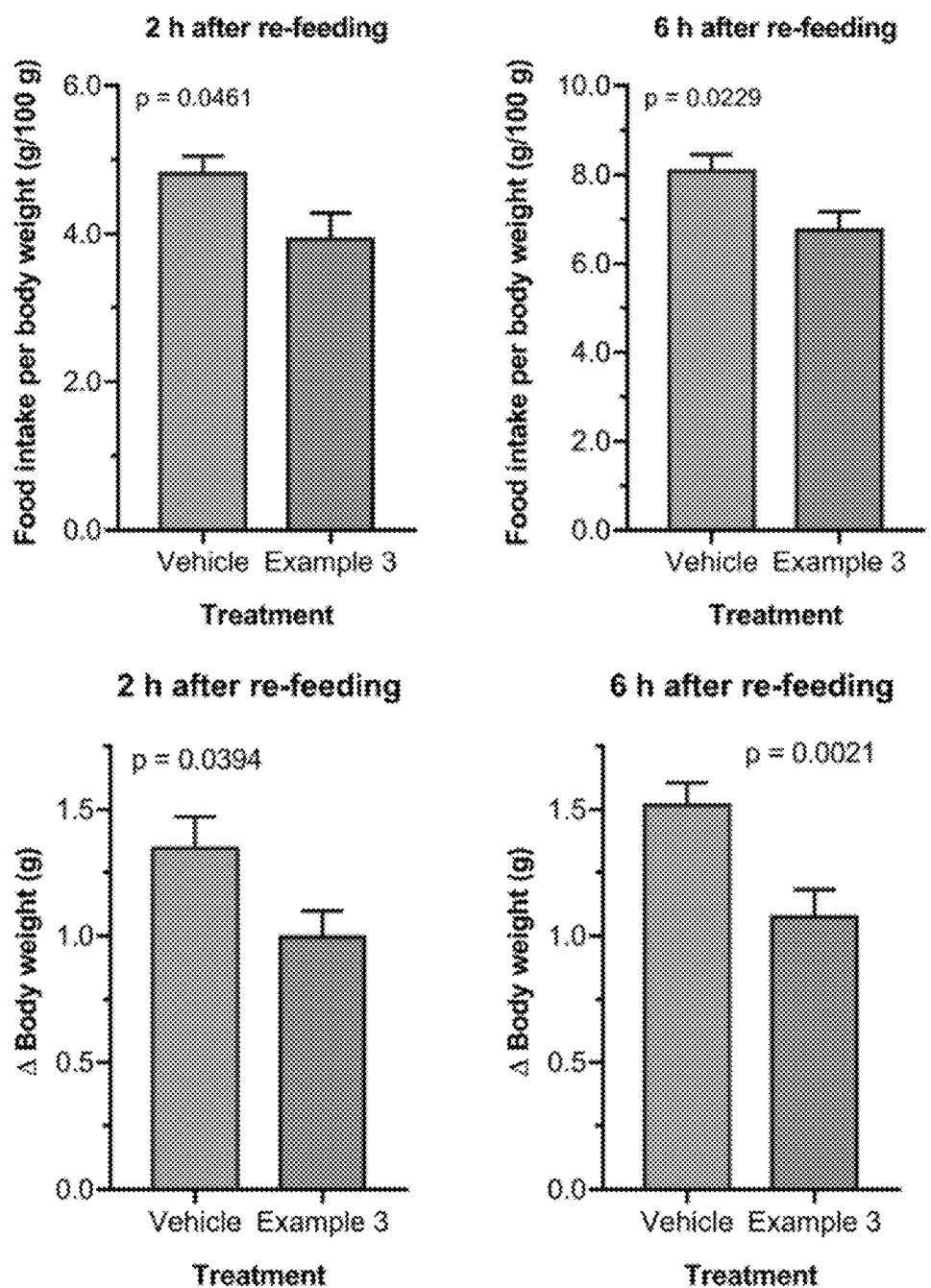
FIG. 4 contains data from assays of inhibition of food intake in the mouse by MC4R PAM Example 3. Nine to ten week old C57BL/6 mice were fasted overnight (15 to 17 hours) and re-feeding was monitored the following day after a single i.p. dose of Example 3 (5 mg/kg) or vehicle (10% Tween 80, 5% DMSO v/v). Normalized food intake (food consumed in grams per 100 grams of body weight) per treatment group is shown in the top graphs after two hours (top left) and six hours (top right) of onset of re-feeding phase. Body weight changes for two and six hours are shown in the bottom left and right panels respectively. p values are noted on each graph and were determined by unpaired t tests. Significance was set to p values <0.05.

High-throughput screening for MC4R positive allosteric modulators based on the 165 hits led to templates containing an indole, and similarity searching around indoles led to a series of 2-acylindoles. Further analogue design and synthesis led to compounds with submicromolar $EC_{50}$s in the positive allosteric modulator assay. Compounds in the series were characterized in vitro, for example Examples 1-3 (FIGS. 2A, 2B, and 2C), and found to have $pEC_{50}$s of 6.4 (Example 1; 83% of αMSH maximal response), 6.3 (Example 2; 80%), and 6.7 (Example 3; 102%). (FIGS. 2A-2I, FIGS. 3A-3F, and FIG. 4). These compounds were also found to exhibit significant specificity for the MC4R, compared with the other melanocortin receptors, and with other Gαs coupled receptors, such as the β2-adrenergic receptor. Functional MC4R is expressed in murine and human intestinal L cells, and inhibits short circuit current in the intestinal epithelium by stimulation of L cell PYY release (Kruse A C, et al. (2013) Activation and allosteric modulation of a muscarinic acetylcholine receptor. *Nature* 504(7478):101-106). To determine if compounds in the indole series could allosterically modulate the native L cell MC4R, their activity on α-MSH induced PYY mediated short circuit current inhibition was studied in mouse colonic epithelium (FIG. 2D). Example 3 had no activity on its own (FIG. 2E), but nearly tripled the activity of α-MSH in this assay (FIG. 2F), with an $EC_{50}$ (~200 nM) comparable to that seen in tissue culture ($pEC_{50}$=6.7). Example 3 did not modulate the activity of PYY (FIG. 2G), and the MC4R antagonist HS014 blocked the allosteric modulation of α-MSH by Example 3 (FIG. 2H), but had no effect on PYY-mediated inhibition of short circuit current (FIG. 2I). Example 1 and Example 2 also exhibited MC4R PAM activity in this assay (FIGS. 3A-3I). The most potent MC4R PAM in this class, Example 3, was also tested for its ability to inhibit fast-induced refeeding in the mouse, and showed a small, but statistically significant anorexigenic activity (FIG. 4).

Example 1

Synthesis of 2-(4-(tert-butyl)piperidin-1-yl)-N-(2-(cyclopropanecarbonyl)-1H-indol-3-yl)acetamide

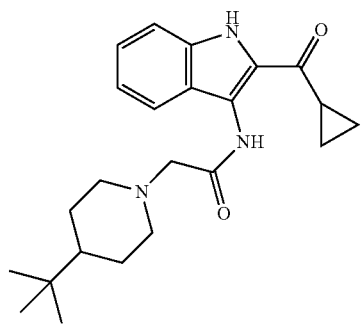 [SMILES: CC(C)(C)C1CCN(CC(=O)Nc2c(C(=O)C3CC3)[nH]c3ccccc23)CC1]

Synthesis of methyl 2-cyanophenylcarbamate: To a stirred solution of 2-aminobenzonitrile (50 g, 423.3 mmol) in pyridine (500 mL) was added methyl chloroformate (48 g, 508.0 mmol) drop wise at 0° C. under inert atmosphere. The reaction mixture was allowed to stir at room temperature for 16 h. After completion of the reaction (monitored by TLC; 0.4 Rf, 30% EtOAc in petroleum ether), pyridine was removed under reduced pressure to obtain the crude product. The crude product was taken in 1N aq. HCl solution (200 mL) and stirred for 1 h. The precipitated solid was filtered, washed with water (2×50 mL), dried by co-distillation with toluene (2×100 mL) to afford methyl 2-cyanophenylcarbamate (44 g, 59%) as a pale yellow solid.

$^1$HNMR (400 MHz, CDCl$_3$): δ 8.23 (d, J=8.3 Hz, 1H), 7.65-7.51 (m, 2H), 7.19-7.07 (m, 2H), 3.83 (s, 3H); LCMS (ESI): m/z 176.9 [M+H$^+$].

Synthesis of 2-bromo-1-cyclopropylethanone: To a stirred solution of cyclopropyl methyl ketone (25 g, 297.6 mmol) in methanol (125 mL) was added bromine (47.5 g, 297.2 mmol) drop wise at 0° C. under inert atmosphere and stirred at same temperature for 2 h. To this, water (125 mL) was added and stirred at room temperature for 16 h. After completion of reaction (monitored by TLC; 0.4 Rf, 10% EtOAc in petroleum ether), the reaction mixture was diluted with water (75 mL) and extracted with diethyl ether (2×250 mL). The combined organic layer was washed with saturated NaHCO$_3$ solution (2×100 mL), brine (100 mL), dried over anhydrous Na$_2$SO$_4$ and evaporated under reduced pressure to afford 2-bromo-1-cyclopropylethanone (40 g) as a colorless oil, which was directly taken for next reaction without further purification.

$^1$HNMR (400 MHz, CDCl$_3$): δ 4.01 (s, 2H), 2.25-2.21 (m, 1H), 1.16-1.12 (m, 2H), 1.05-0.98 (m, 2H); GCMS: m/z 162 [M$^+$]; RT=5.09 min (ZB-5MS column; 100° C./1 min, 20° C./min/310° C./5 min).

Synthesis of (3-amino-1H-indol-2-yl)(cyclopropyl)methanone: To a stirred solution of Methyl 2-cyanophenylcarbamate (20 g, 113.5 mmol) in DMF (200 mL) was added 2-bromo-1-cyclopropylethanone (27.75 g) followed by aqueous KOH solution (31.84 g, 567.5 mmol; in 200 ml water) at 0° C. under inert atmosphere. The reaction mixture was heated to 80° C. and stirred for 6 h. The reaction was monitored by TLC (0.35 Rf, 30% EtOAc in petroleum ether). After completion of reaction, the reaction mixture was cooled to room temperature, quenched with ice-cold water (150 mL) and extracted with EtOAc (3×150 mL). The combined organic layer was washed with ice-cold water (150 mL), brine (150 mL), dried over anhydrous Na$_2$SO$_4$ and concentrated under reduced pressure. The crude product was purified by silica gel column chromatography (100-200 mesh) using 20% EtOAc in petroleum ether to afford (3-amino-1H-indol-2-yl)(cyclopropyl)methanone (6 g, 26%) as a brown solid.

$^1$HNMR (400 MHz, CDCl$_3$): δ 7.68 (br s, 1H), 7.58 (d, J=8.1 Hz, 1H), 7.40-7.32 (m, 1H), 7.31-7.27 (m, 1H), 7.09-7.05 (m, 1H), 5.39 (br s, 2H), 2.27-2.19 (m, 1H), 1.28-1.24 (m, 2H), 1.01-0.96 (m, 2H); LCMS (ESI): m/z 201.1 [M+H$^+$].

Synthesis of 2-chloro-N-(2-(cyclopropanecarbonyl)-1H-indol-3-yl)acetamide: To a stirred solution of (3-amino-1H-indol-2-yl)(cyclopropyl)methanone (3.5 g, 17.48 mmol) in CH$_2$Cl$_2$ (200 mL) was added triethylamine (9.8 mL, 69.92 mmol) followed by 2-chloroacetyl chloride (1.8 mL, 22.72 mmol) at −5° C. under inert atmosphere. The reaction allowed to warm to room temperature and stirred for 48 h. After completion of reaction (monitored by TLC; 0.35 Rf, 50% EtOAc in petroleum ether), the precipitated solid was filtered, washed with n-pentane (280 mL) and dried under vacuum to afford 2-chloro-N-(2-(cyclopropanecarbonyl)-1H-indol-3-yl)acetamide (1.8 g, 37%) as an off-white solid.

$^1$HNMR (400 MHz, CDCl$_3$): δ 10.38 (br s, 1H), 8.60 (br s, 1H), 8.16 (d, J=8.1 Hz, 1H), 7.43-7.34 (m, 2H), 7.19-7.15 (m, 1H), 4.29 (s, 2H), 2.44-2.39 (m, 1H), 1.40-1.33 (m, 2H), 1.14-1.09 (m, 2H); LCMS (ESI): m/z 277.1 [M+H$^+$].

Synthesis of 2-(4-tert-butylpiperidin-1-yl)-N-(2-(cyclopropanecarbonyl)-1H-indol-3-yl)acetamide: To a stirred solution of 2-chloro-N-(2-(cyclopropanecarbonyl)-1H-indol-3-yl)acetamide (800 mg, 2.89 mmol) in acetonitrile (150 mL) was added diisopropyl ethylamine (2.51 mL, 14.45 mmol) and 4-tert-butylpiperidine hydrochloride (614 mg, 3.46 mmol) at 0° C. under inert atmosphere. The reaction mixture was stirred at room temperature for 48 h. The progress of reaction was monitored by TLC (0.35 Rf, 40% EtOAc in petroleum ether). After completion of reaction, the reaction mixture was poured into ice-cold water (65 mL) and extracted with CH$_2$Cl$_2$ (3×150 mL). The combined organic layer was washed with brine (50 mL), dried over anhydrous Na$_2$SO$_4$ and concentrated under reduced pressure to afford the crude product.

The reaction was repeated on 400 mg scale and both the crude materials were combined and purified through reverse phase preparative HPLC (XBridge C18 column; 0.01M aq. ammonium bicarbonate with MeCN). The appropriate fractions were lyophilized to afford 2-(4-tert-butylpiperidin-1-yl)-N-(2-(cyclopropanecarbonyl)-1H-indol-3-yl)acetamide (780 mg, 47%) as an off-white solid.

$^1$HNMR (400 MHz, CDCl$_3$): δ 10.26 (br s, 1H; D$_2$O exchangeable), 8.73 (br s, 1H; D$_2$O exchangeable), 8.00 (d, J=8.3 Hz, 1H), 7.39-7.31 (m, 2H), 7.16-7.12 (m, 1H), 3.22 (s, 2H), 3.06-3.03 (m, 2H), 2.54-2.42 (m, 1H), 2.25 (dt, J=11.7, 2.2 Hz, 2H), 1.72-1.69 (m, 2H), 1.46 (dq, J=12.4, 3.7 Hz, 2H), 1.34-1.26 (m, 2H), 1.05-1.01 (m, 3H), 0.89 (s, 9H); LCMS (ESI): m/z 382.1 [M+H$^+$].

Example 2

Synthesis of N-(2-(cyclopropanecarbonyl)-1H-indol-3-yl)-2-(8-azaspiro[4.5]decan-8-yl)acetamide

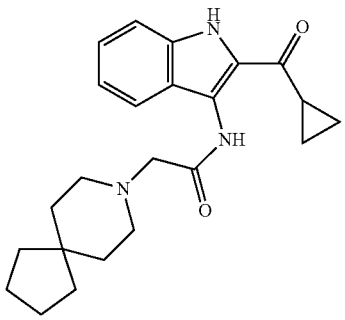 [SMILES: O=C(CN1CCC2(CCCC2)CC1)Nc1c(C(=O)C2CC2)[nH]c2ccccc12]

To a stirred solution of 2-chloro-N-(2-(cyclopropanecarbonyl)-1H-indol-3-yl)acetamide (see Example 1; 1.2 g, 3.34 mmol) in dichloromethane (100 mL) was added triethylamine (2.51 mL, 14.45 mmol) and 8-azaspiro[4.5]decane (724 mg, 5.2 mmol) at 0° C. under inert atmosphere. The reaction mixture was stirred at room temperature for 72 h. The progress of reaction was monitored by TLC (0.3 Rf; 50% EtOAc in petroleum ether). After completion of reaction, the reaction mixture was poured into ice-cold water (100 mL) and extracted with $CH_2Cl_2$ (3×150 mL). The combined organic layer was washed with brine (50 mL), dried over anhydrous $Na_2SO_4$ and concentrated under reduced pressure to afford the crude product.

Purified through reverse phase preparative HPLC (XBridge C18 column; 10 mM aq. ammonium bicarbonate with MeCN). The appropriate fractions were lyophilized to afford N-(2-(cyclopropanecarbonyl)-1H-indol-3-yl)-2-(8-azaspiro[4.5]decan-8-yl)acetamide (569 mg, 34%) as an off-white solid.

$^1$H NMR (400 MHz, DMSO-$d_6$): δ 11.78 (s, 1H; $D_2O$ exchangeable), 10.81 (s, 1H; $D_2O$ exchangeable), 8.04 (d, J=8.3 Hz, 1H), 7.49-7.38 (m, 1H), 7.30 (ddd, J=8.3, 7.0, 1.2 Hz, 1H), 7.02 (ddd, J=8.3, 7.0, 1.2 Hz, 1H), 3.14 (s, 2H), 2.84-2.70 (m, 1H), 2.50-2.47 (m, 4H), 1.64-1.49 (m, 8H), 1.45-1.37 (m, 4H), 1.15-0.96 (m, 4H); LCMS (ESI): m/z 380.09 [M+H$^+$].

Example 3

Synthesis of methyl 3-(2-(4-cyclohexylpiperidin-1-yl)acetamido)-1H-indole-2-carboxylate

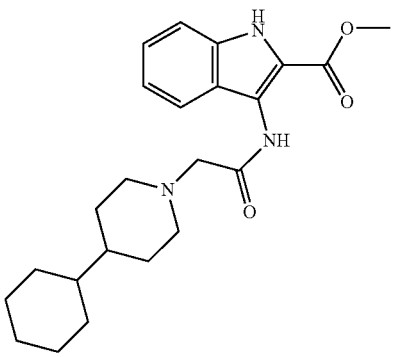 [SMILES: COC(=O)c1[nH]c2ccccc2c1NC(=O)CN1CCC(C2CCCCC2)CC1]

Synthesis of methyl 3-amino-1H-indole-2-carboxylate: To a stirred solution of 2-aminobenzonitrile (20 g, 169.1 mmol) in DMF (200 mL) was added potassium carbonate (70.13 g, 507.4 mmol) followed by methyl bromoacetate (24.25 mL, 253.7 mmol) at room temperature under inert atmosphere. The reaction mixture was heated to 100° C. and stirred for 16 h. The progress of reaction was monitored by TLC (0.25 Rf; 30% EtOAc in petroleum ether). After completion of reaction, the reaction mixture was cooled to room temperature and diluted with EtOAc (1.5 Lt). The resultant organic solution was washed with ice-cold water (2×500 mL), brine (250 mL), dried over anhydrous $Na_2SO_4$ and concentrated under reduced pressure to obtain the crude product, which was purified by silica gel column chromatography (100-200 mesh; 15-20% EtOAc gradient in petroleum ether) to afford methyl 3-amino-1H-indole-2-carboxylate (4.5 g, 14%) as an off-white solid.

$^1$HNMR (400 MHz, DMSO-$d_6$): δ 10.35 (s, 1H), 7.74 (d, J=8.1 Hz, 1H), 7.25-7.15 (m, 2H), 6.93-6.83 (m, 1H), 5.68 (br s, 2H), 3.81 (s, 3H); LCMS (ESI): m/z 191.1 [M+H$^+$].

Synthesis of methyl 3-(2-chloroacetamido)-1H-indole-2-carboxylate: To a stirred solution of methyl 3-amino-1H-indole-2-carboxylate (2.5 g, 13.14 mmol) in $CH_2Cl_2$ (100 mL) was added triethylamine (3.4 mL, 26.28 mmol) followed by 2-chloroacetyl chloride (1.3 mL, 17.08 mmol) at 0° C. under inert atmosphere. The reaction mixture was allowed to stir at room temperature for 16 h. The progress of reaction was monitored by TLC (0.3 Rf; 30% EtOAc in petroleum ether). After completion of reaction, the reaction mixture was diluted with $CH_2Cl_2$ (500 mL). The resultant organic solution was washed with water (3×100 mL), brine (50 mL), dried over anhydrous $Na_2SO_4$ and concentrated under reduced pressure to afford methyl 3-(2-chloroacetamido)-1H-indole-2-carboxylate (2.2 g, 63%) as an off-white solid.

$^1$HNMR (400 MHz, DMSO-$d_6$): δ 11.84 (br s, 1H), 10.01 (br s, 1H), 7.61 (d, J=8.1 Hz, 1H), 7.41 (d, J=8.1 Hz, 1H), 7.28 (t, J=8.1 Hz, 1H), 7.06 (t, J=8.1 Hz, 1H), 4.39 (s, 2H), 3.87 (s, 3H); LCMS (ESI): m/z 267.1 [M+H$^+$].

Synthesis of 4-cyclohexylpiperidine hydrochloride: To a solution of 4-phenylpyridine (5 g, 32.21 mmol) in ethanol (250 mL) and concentrated HCl solution (50 mL), was added $PtO_2$ (880 mg, 3.86 mmol) at room temperature under inert atmosphere. The reaction was stirred under hydrogen atmosphere (55 psi pressure; Parr Shaker hydrogenator) for 4 days. The progress of reaction was monitored by proton NMR analysis. After completion of reaction, the reaction mixture was diluted with ethanol (100 mL) and filtered through a celite pad. The filtrate was concentrated under reduced pressure to obtain the residue, which was dissolved in $CH_2Cl_2$ (200 mL) and filtered again. The filtrate was concentrated under reduced pressure to afford 4-cyclohexylpiperidine hydrochloride (5 g) as a pale green solid, which was directly taken for next reaction without further purification.

$^1$HNMR (400 MHz, DMSO-$d_6$): δ 8.84 (br s, 1H), 8.59 (br s, 1H), 3.45-3.41 (m, 2H), 3.23-3.19 (m, 2H), 2.76-2.74 (m, 2H), 1.81-1.51 (m, 6H), 1.36-1.32 (m, 3H), 1.16-1.13 (m, 3H), 0.95-0.89 (m, 2H); GCMS: m/z 167.2 [M$^+$].

Synthesis of methyl 3-(2-(4-cyclohexylpiperidin-1-yl)acetamido)-1H-indole-2-carboxylate: To a stirred solution of methyl 3-(2-chloroacetamido)-1H-indole-2-carboxylate (1.5 g, 5.63 mmol) in acetonitrile (200 mL) was added caesium carbonate (3.7 g, 11.38 mmol) followed by 4-cyclohexylpiperidine hydrochloride (1.41 g) at room temperature under inert atmosphere and stirred for 16 h. The progress of reaction was monitored by TLC (0.5 Rf; 50% EtOAc in petroleum ether). After completion of reaction, the reaction mixture was diluted with EtOAc (200 mL) and filtered the inorganic salts. The filtrate was washed with water (2×50 mL), dried over anhydrous $Na_2SO_4$ and concentrated under reduced pressure. The obtained crude product was purified by reverse phase preparative HPLC (Sunfire C18 column; 0.1% aq. HCOOH with acetonitrile). The appropriate fractions were combined and concentrated to ¼$^{th}$ of its volume and then neutralized with saturated $NaHCO_3$ solution (2 mL). The resultant solution was extracted with $CH_2Cl_2$ (100 mL). The $CH_2Cl_2$ layer was concentrated under reduced pressure and dried under vacuum to afford methyl 3-(2-(4-cyclohexylpiperidin-1-yl)acetamido)-1H-indole-2-carboxylate (588 mg, 26%) as an off-white solid.

$^1$HNMR (400 MHz, $CDCl_3$): δ 10.31 (br s, 1H; $D_2O$ exchangeable), 8.49 (br s, 1H; $D_2O$ exchangeable), 8.22 (d, J=8.3 Hz, 1H), 7.37-7.27 (m, 2H), 7.12 (ddd, J=8.3, 6.3, 1.9 Hz, 1H), 3.98 (s, 3H), 3.20 (s, 2H), 3.06-3.01 (m, 2H), 2.23 (dt, J=11.7, 2.4 Hz, 2H), 1.82-1.62 (m, 7H), 1.47 (dq, J=12.2, 3.7 Hz, 2H), 1.30-1.05 (m, 5H), 1.03-0.94 (m, 2H); LCMS (ESI): m/z 398.1 [M+H$^+$].

PAM HTS Screen and Counter Screen

In order to identify PAMS of the hMC4R an assay described in Pantel J, et al. (2011) Development of a high throughput screen for allosteric modulators of melanocortin-4 receptor signaling using a real time cAMP assay. *Eur J Pharmacol* 660:139-147, was followed. This assay allowed recordation of intracellular cAMP concentration kinetics in live cells.

HEK293 cells stably expressing the hMC4R or the β-adrenergic receptor with the p-Promega pGlo luciferase cAMP reporter were plated at a density of 10,000 to 15,000 cells per well on Poly-D-Lysin coated black optical bottom 384 well plates in MEM supplemented with 2% serum. The next day, cells were loaded with the p-Glo substrate at a 2% concentration in $CO_2$-independent media for 2 hours at 37° C. cAMP concentration in cells were measured as a function of luminescence over time using a Hamamatsu FDSS 6000 plate reader. Basal luminescence were measured for 5 minutes followed by injection of 1 μM of the library compounds. Signal after the first injection was monitored for 5 minutes as a way to measure if compounds have any activity on their own. After 5 minutes a submaximal concentration approaching the $EC_{20}$ of the natural hMC4R agonist α-MSH was added and the cAMP mediated luminescence signal was recorded for another 10 minutes (FIG. 1A).

Using this assay, 150,981 compounds from the Vanderbilt Institute for Chemical Biology (VICB) small molecule collection were screened and 2472 hits with either orthosteric or allosteric activity were identified. 1816 compounds were defined as allosteric in nature (FIG. 1A) in that they did not significantly raise cAMP production when injected on their own, but potentiated cAMP production only in the presence of the α-MSH $EC_{20}$ stimulus.

Because those molecules can potentially act at several points in the cAMP pathway downstream of the receptor, for example as phosphodiesterase inhibitors, all 1,816 allosteric compounds were counter screened in a cell line expressing the pGLO reporter along with the human β2-adrenergic receptor, another Gas coupled receptor. 165 compounds, or 0.1% of total compounds screened, enhanced hMC4R signaling with no significant effect on β2-adrenergic-receptor signaling. An example of the primary kinetic screen data from one such compound, VUO127431 (N-(furan-2-ylmethyl)-2-(3,4,5-trimethoxyphenyl)quinazolin-4-amine), is illustrated in FIGS. 1B and 1C. A summary of the outcome of the screen is indicated in FIG. 1D.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A compound selected from the group consisting of

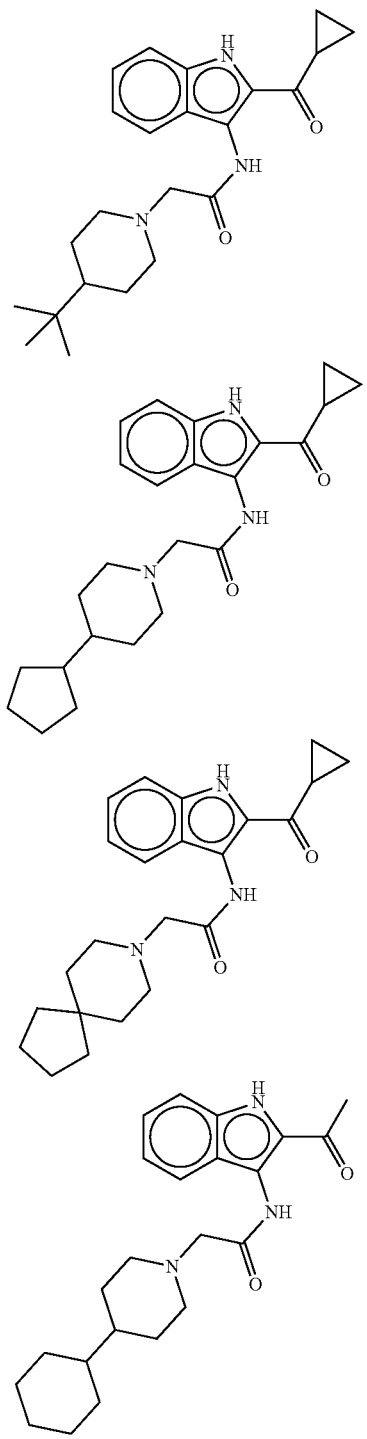

-continued
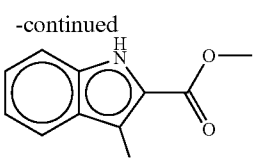
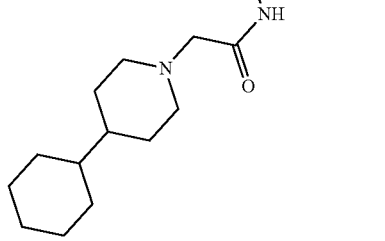
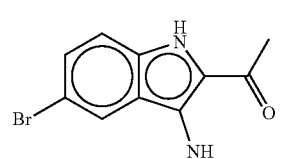
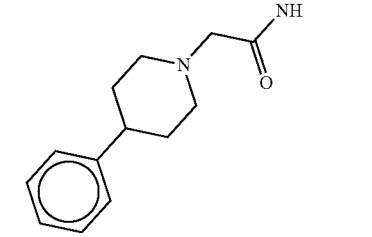
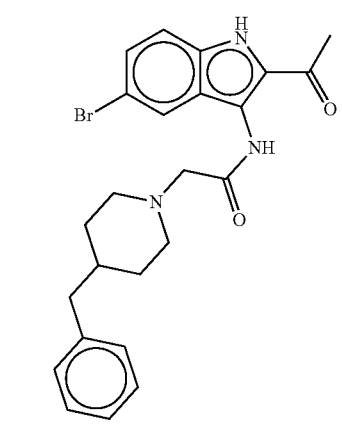
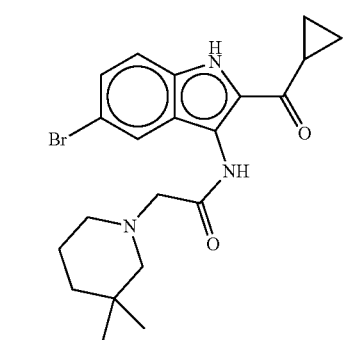
-continued
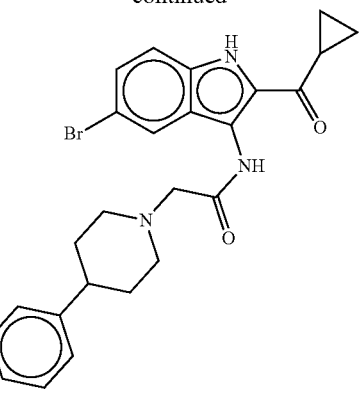
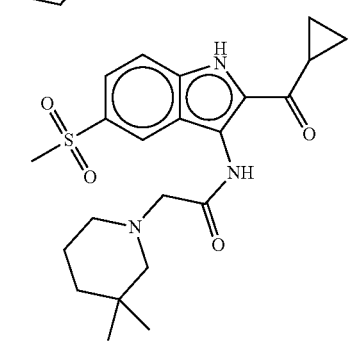
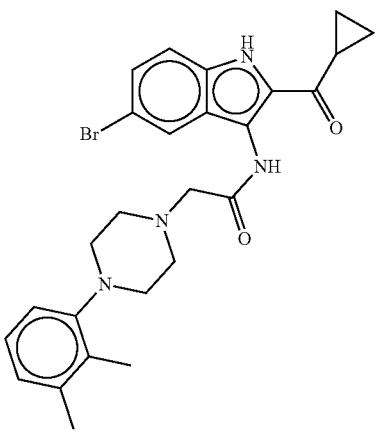
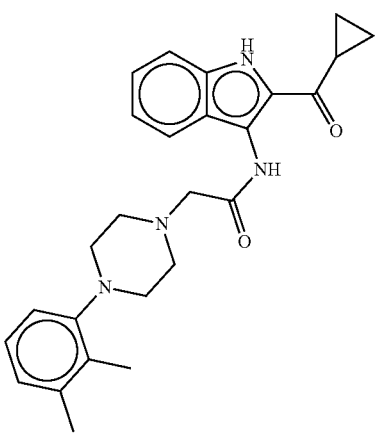

81
-continued
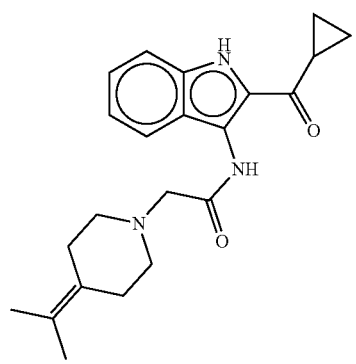
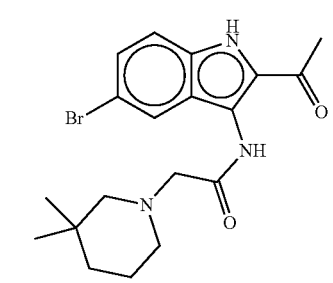
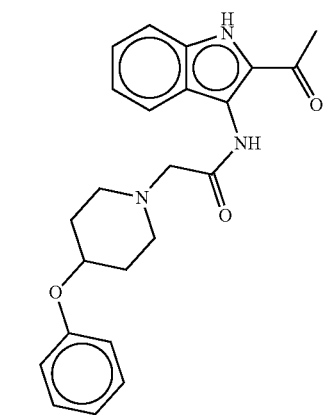
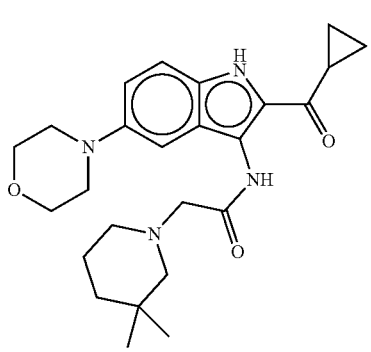
82
-continued
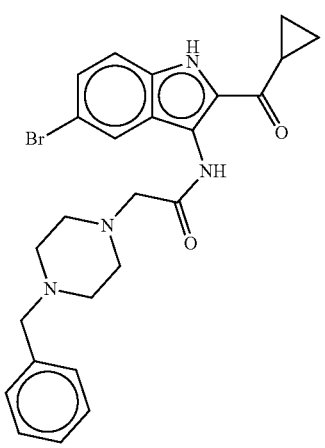
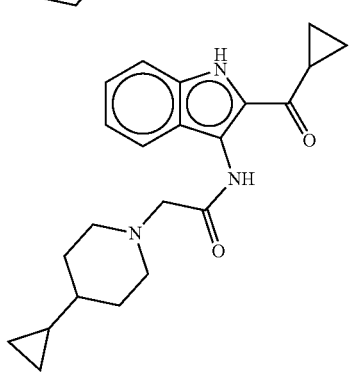
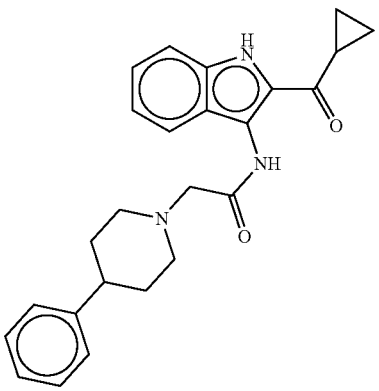
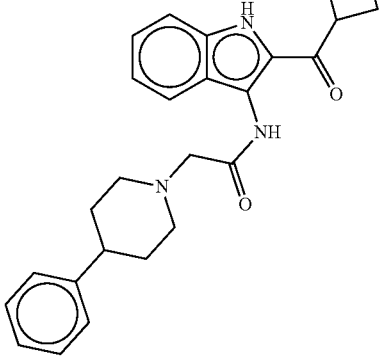

83
-continued
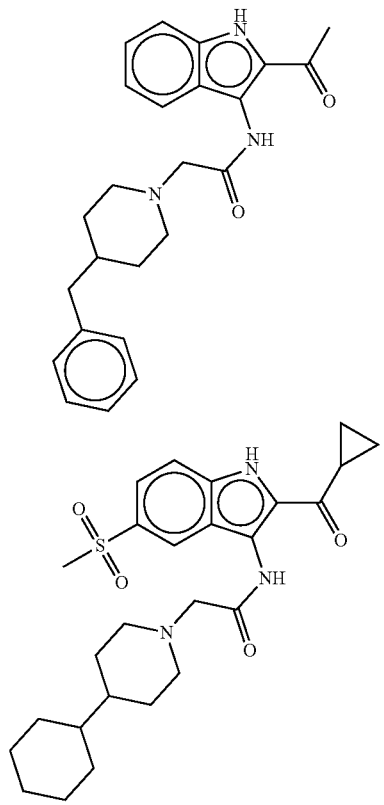
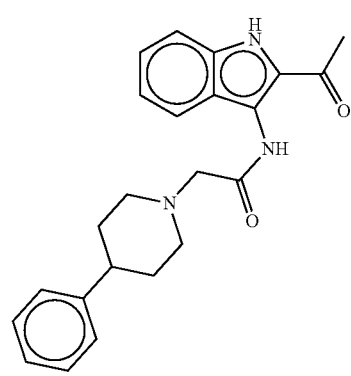
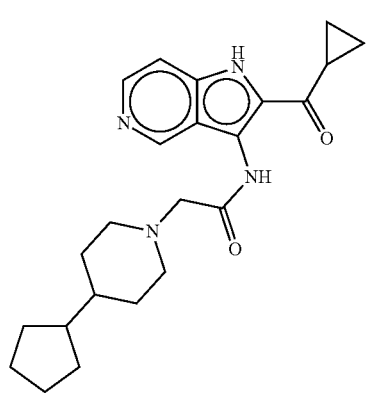
84
-continued
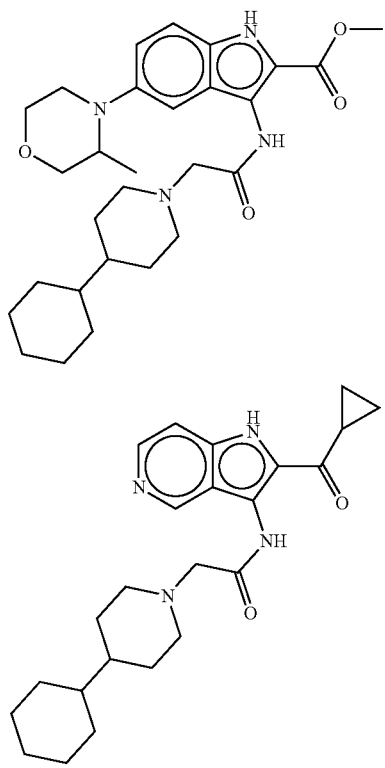
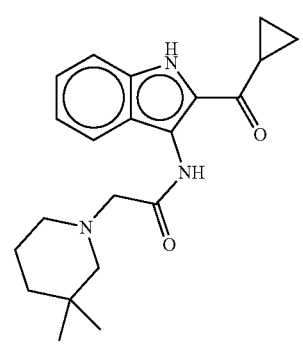
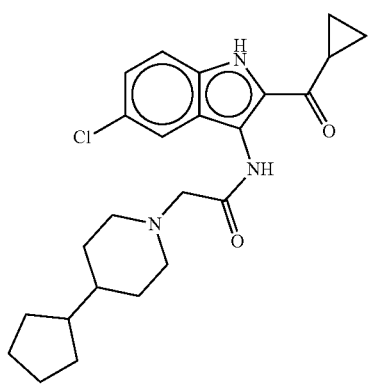

85
-continued
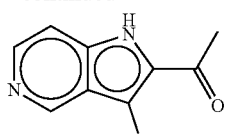
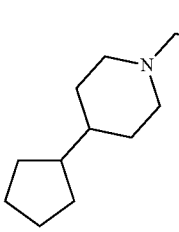
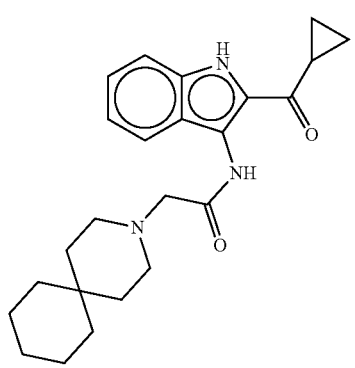
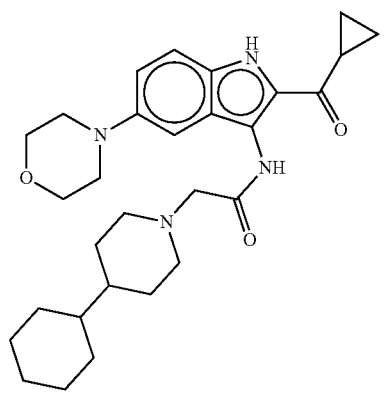
86
-continued
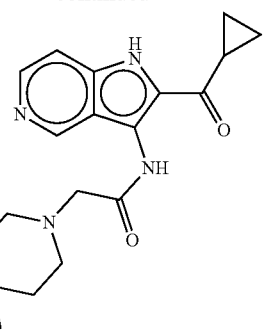
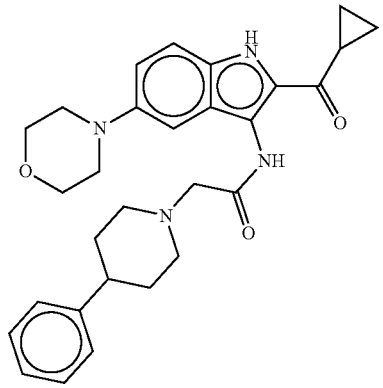
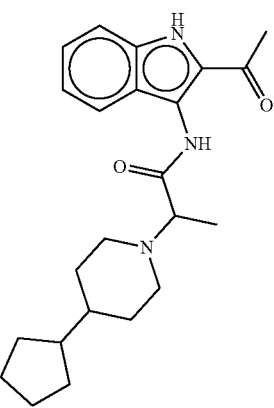

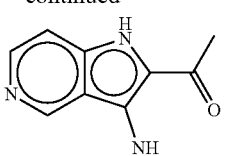
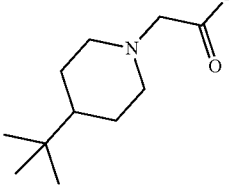
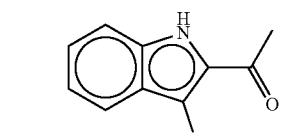
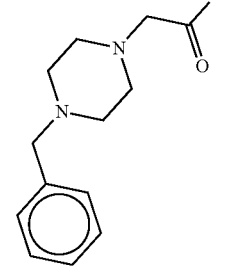
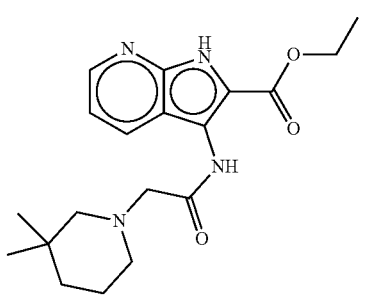
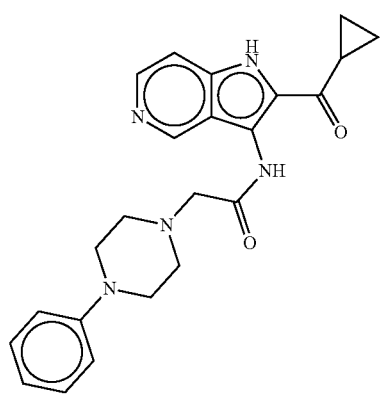
and
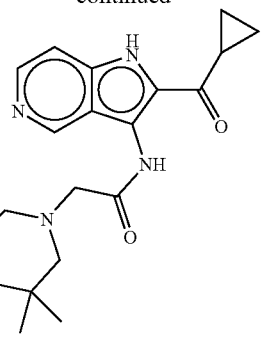
or a pharmaceutically acceptable salt thereof.
2. A pharmaceutical composition, comprising: the compound claim 1 and a pharmaceutically acceptable carrier.
3. A compound of clam 1, wherein the compound is
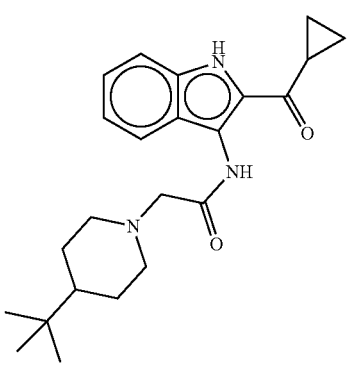
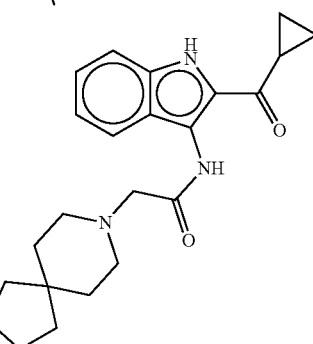
or
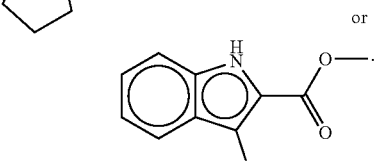
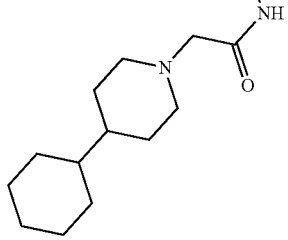
\* \* \* \* \*